(12) United States Patent
Zhang et al.

(10) Patent No.: US 11,450,423 B2
(45) Date of Patent: Sep. 20, 2022

(54) SYSTEM AND METHOD FOR PROCESSING MEDICAL IMAGE DATA

(71) Applicant: SHANGHAI UNITED IMAGING HEALTHCARE CO., LTD., Shanghai (CN)

(72) Inventors: Zhongqi Zhang, Shanghai (CN); Anling Ma, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 109 days.

(21) Appl. No.: 16/202,146

(22) Filed: Nov. 28, 2018

(65) Prior Publication Data

US 2019/0108905 A1 Apr. 11, 2019

Related U.S. Application Data

(63) Continuation of application No. PCT/CN2017/082349, filed on Apr. 28, 2017.

(30) Foreign Application Priority Data

Dec. 26, 2016 (CN) .......................... 201611216412.4

(51) Int. Cl.
*G16H 30/20* (2018.01)
*G16H 30/40* (2018.01)
(Continued)

(52) U.S. Cl.
CPC ......... *G16H 30/20* (2018.01); *G06F 9/44505* (2013.01); *G06T 7/0012* (2013.01); *G16H 30/40* (2018.01); *G16H 40/63* (2018.01)

(58) Field of Classification Search
CPC .................. G16H 30/00–40; G06F 19/321
See application file for complete search history.

(56) References Cited

U.S. PATENT DOCUMENTS

| | | | |
|---|---|---|---|
| 2002/0016718 A1* | 2/2002 | Rothschild | H04N 1/32128 705/2 |
| 2005/0121505 A1* | 6/2005 | Metz | G16H 30/20 235/375 |
| 2006/0198552 A1* | 9/2006 | Spahn | G06T 5/40 382/128 |

(Continued)

FOREIGN PATENT DOCUMENTS

| | | |
|---|---|---|
| CN | 1787447 A | 6/2006 |
| CN | 1794246 A | 6/2006 |

(Continued)

OTHER PUBLICATIONS

International Search Report in PCT/CN2017/082349 dated Sep. 28, 2017, 7 pages.

(Continued)

*Primary Examiner* — Vincent Rudolph
*Assistant Examiner* — Raphael Schwartz
(74) *Attorney, Agent, or Firm* — Metis IP LLC

(57) ABSTRACT

This disclosure provides a system and a method. The method may include: determining a processing instruction; acquiring image data based on the processing instruction; determining a configuration file based on the image data, in which the configuration file may be configured to guide implementation of the processing instruction; constructing a data processing pipeline based on the configuration file; executing the data processing process based on the data processing pipeline, in which the data processing process may be generated based on the data processing pipeline; generating a processing result of the image data based on the executed data processing process; and storing the processing result of the image data in a first storage space.

20 Claims, 17 Drawing Sheets

(51) Int. Cl.
    *G06F 9/445*     (2018.01)
    *G16H 40/63*     (2018.01)
    *G06T 7/00*     (2017.01)

(56) References Cited

U.S. PATENT DOCUMENTS

| | | | |
|---|---|---|---|
| 2007/0063998 A1* | 3/2007 | Mahesh | G06F 3/0482 |
| | | | 345/419 |
| 2007/0124541 A1* | 5/2007 | Lang | G06F 12/0862 |
| | | | 711/137 |
| 2008/0133596 A1* | 6/2008 | Chang | G06F 19/321 |
| 2013/0208964 A1 | 8/2013 | Dwivedi | |
| 2015/0123810 A1* | 5/2015 | Hernandez-Rosas | |
| | | | A61B 5/14503 |
| | | | 340/870.02 |
| 2015/0379677 A1 | 12/2015 | Chen et al. | |
| 2017/0243332 A1* | 8/2017 | Takahashi | G06T 5/003 |
| 2017/0337672 A1 | 11/2017 | Zou et al. | |

FOREIGN PATENT DOCUMENTS

| | | |
|---|---|---|
| CN | 101777012 A | 7/2010 |
| CN | 103530855 A | 1/2014 |
| CN | 103886167 A | 6/2014 |
| CN | 104598212 A | 5/2015 |

OTHER PUBLICATIONS

First Office Action in Chinese Application No. 201611216412.4 dated Jan. 10, 2018, 15 pages.

* cited by examiner

SYSTEM AND METHOD FOR PROCESSING MEDICAL IMAGE DATA

CROSS-REFERENCE TO RELATED APPLICATIONS

This present application is a continuation of International Application No. PCT/CN2017/082349, filed on Apr. 28, 2017, which claims priority to Chinese Application No. 201611216412.4, filed on Dec. 26, 2016, the entire contents of which are hereby incorporated by reference.

TECHNICAL FIELD

The present disclosure generally relates to information processing technology, and more particularly, relates to a method and system for processing image data.

BACKGROUND

A hospital information system (HIS) may include a medical picture archiving and communication system (PACS), a clinical information system (CIS), a radiology information system (RIS), a laboratory information system (LIS), or the like. In medical industry, the medical picture archiving and communication system (PACS) may include the radiology information system (RIS). The data format of the data in the PACS may satisfy an international standard (e.g., digital imaging and communication in medicine (DICOM)). The PACS may store and/or manage data and/or image based on one or more databases. The PACS may be a comprehensive system having one or more functions including image/data collection, image/data transmission, image/data storage, image/data management, image diagnosis, data query, report management, comprehensive information management, or the like. The PACS may store, process, and/or analyze various medical images (e.g., a magnetic resonance (MR) image, a computed tomography (CT) image, a positron emission tomography (PET) image, an ultrasound image, an image generated by a digital radiography (DR) system, an image generated by an X-ray-based device, etc.) based on the international standard (e.g., DICOM).

With the improvement of the medical technology and the development of patients' requirement, in order to accurately detect lesion area and nature in the patients' body, a user (e.g., a doctor) may scan local or systemic body of a patient with a high accuracy, and determine diagnosis and/or treatment schemes based on the corresponding scan result (e.g., an image). The data acquired by scanning may need to be processed to help the doctor view the image and diagnose diseases. The doctor may process the image while observing the image via, e.g., the PACS, and one or more diagnosis reports may be generated. However, since there are a large amount of image data, it takes the doctor a relatively long time to wait the image processing process to be performed when the doctor is viewing the image. Therefore, it is desirable to provide a system and method for processing medical image data to improve the efficiency of obtaining an image processing result by a user terminal, so that a fast query, extraction, image-viewing, transmission, display, or the like of the medical image may be realized in real time, the doctor' time spent for viewing images may be saved, and accordingly, the user experience may be improved.

SUMMARY

An aspect of the present disclosure relates to a method for processing medical image data. The method for processing the medical image data may include: determining a processing instruction; acquiring image data based on the processing instruction; determining a configuration file based on the image data; constructing a data processing pipeline based on the configuration file; executing a data processing process based on the data processing pipeline; generating a processing result of the image data based on the executed data processing process; and storing the processing result of the image data in a first storage space. In some embodiments, the configuration file may be configured to guide implementation of the processing instruction. In some embodiments, the data processing process may be generated based on the data processing pipeline.

Another aspect of the present disclosure relates to a non-transitory computer readable medium. The non-transitory computer readable medium may include executable instructions. The instructions may be executed by at least one processor, causing the at least one processor to effectuate the method for processing the medical image data.

Another aspect of the present disclosure relates to a system for processing medical image data. The system may include: a human-computer interaction module configured for receiving a processing instruction; a data acquisition module configured for acquiring image data; a configuration file determination unit configured for determining a configuration file; a pipeline construction unit configured for constructing a data processing pipeline, the data processing pipeline may include at least one data source filter, a plurality of pipes at least one filter, and at least one data root filter; a data processing module configured for executing a data processing process to generate a processing result of the image data; and a data storage module configured for storing the processing result of the image data into a first storage space.

According to some embodiments of the present disclosure, the determining the processing instruction may include receiving the processing instruction.

According to some embodiments of the present disclosure, the determining the processing instruction may include receiving information relating to a medical image; and determining the processing instruction by analyzing the information.

According to some embodiments of the present disclosure, the determining the configuration file may include: determining whether there is a matched configuration file based on a type of the image data; and in response to a determination that there is a matched configuration file, determining the matched configuration file as the configuration file; in response to a determination that there is no matched configuration file, determining a scan protocol relating to the image data; and generating the configuration file based on the scan protocol.

According to some embodiments of the present disclosure, the method for processing the medical image data may further include storing the configuration file into a second storage space.

According to some embodiments of the present disclosure, the configuration file may include a name of a first filter, and a connection manner of the first filter with at least one data source filter and at least one data root filter, and wherein the constructing the data processing pipeline may include: forming the data processing pipeline based on the first filter, the at least one data source filter, the at least one data root filter, the connection manner, and a plurality of pipes, in which the data processing pipeline may include the first filter, the at least one data source filter, the at least one data root filter, and the plurality of pipes; and the plurality of pipes may connect the at least one data source filter, the first filter, and the at least one data root filter based on the connection manner.

According to some embodiments of the present disclosure, the first filter ay be configured with an algorithm for processing the image data.

According to some embodiments of the present disclosure, the method for processing the medical image data may further include adding a name of a second filter, modifying the name of the first filter, or modifying the connection manner in the configuration file.

According to some embodiments of the present disclosure, the method for processing the medical image data may further include monitoring a memory resource occupied by the data processing process.

According to some embodiments of the present disclosure, the method for processing the medical image data may further include: generating a folder based on a storage location of the image data in the first storage space, the folder may be used for storing information relating to the data processing process.

According to some embodiments of the present disclosure, the storing the processing result of the image data may include: storing the processing result of the image data based on a digital imaging and communications in medicine (DICOM) standard.

According to some embodiments of the present disclosure, the executing the data processing process may include: executing at least two data processing processes simultaneously, in which the at least two data processing processes may be executed independently.

According to some embodiments of the present disclosure, the method for processing the medical image data may further include: determining whether the data processing process terminates with an exception; and in response to a determination that the data processing process terminates with an exception, deleting the processing result of the image data.

According to some embodiments of the present disclosure, the storing the processing result of the image data into the first storage space may further include: converting the processing result of the image data to obtain a converted result; and storing the converted result in the first storage space.

BRIEF DESCRIPTION OF THE DRAWINGS

In order to make the technical solution of the exemplary embodiments of the present disclosure more clearly, these exemplary embodiments are described in detail with reference to the drawings. It is obvious that drawings in the following description are only some examples or embodiments of the present disclosure. The present disclosure may be applied to the other similar scenario according to these drawings for those skilled in the art without paying creative efforts. Unless it will be obvious from the language environment or otherwise is specified herein, like reference numerals in the figures represent the same structures or the same operation.

DETAILED DESCRIPTION

As described in the specification and claims, the singular forms "a," "an," and "the" may be intended to include the plural forms as well, unless the context clearly indicates otherwise. It will be further understood that the terms "comprises," "comprising," "includes," and/or "including" when used in this disclosure, specify the presence of stated steps and elements, but do not preclude the presence or addition of one or more other steps and elements.

Some modules of the image processing system may be referred to in various ways according to some embodiments of the present disclosure, however, any number of different modules may be used and operated in an electric control equipment. These modules are intended to be illustrative, not intended to limit the scope of the present disclosure. Different modules may be used in different aspects of the system and method.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flowcharts, or one or more operations may be omitted from the flowchart.

In the system for processing the medical image data, the medical images may include one or more images generated by one or more imaging technologies. The imaging technology may include a digital subtraction angiography (DSA), a magnetic resonance imaging (MRI), a magnetic resonance angiography (MRA), a computed tomography (CT), a computed tomography angiography (CTA), a ultrasound scanning (US), a positron emission tomography (PET), a single-photon emission computerized tomography (SPECT), a SPECT-MR, a CT-PET, a CE-SPECT, a DSA-MR, a PET-MR, a PET-US, a SPECT-US, a transcranial magnetic stimulation-MR (TMS-MR), a US-CT, a US-MR, an X-ray CT, an X-ray PET, an X-ray US, or the like, or a combination thereof.

In some embodiments, an object displayed in the medical image may include an organ, an organism, a substance, an injured site, a tumor, or the like, or a combination thereof. In some embodiments, the object displayed in the medical image may include one or more diseased tissues of a body. In some embodiments, the medical image may be a two-dimensional image and/or a three-dimensional image. In the two-dimensional image, its tiniest distinguishable element may be referred to as a pixel. In the three-dimensional image, its tiniest distinguishable element may be referred to as a voxel. The three-dimensional image may include a series of two-dimensional slices or two-dimensional image layers.

Figure 1A:
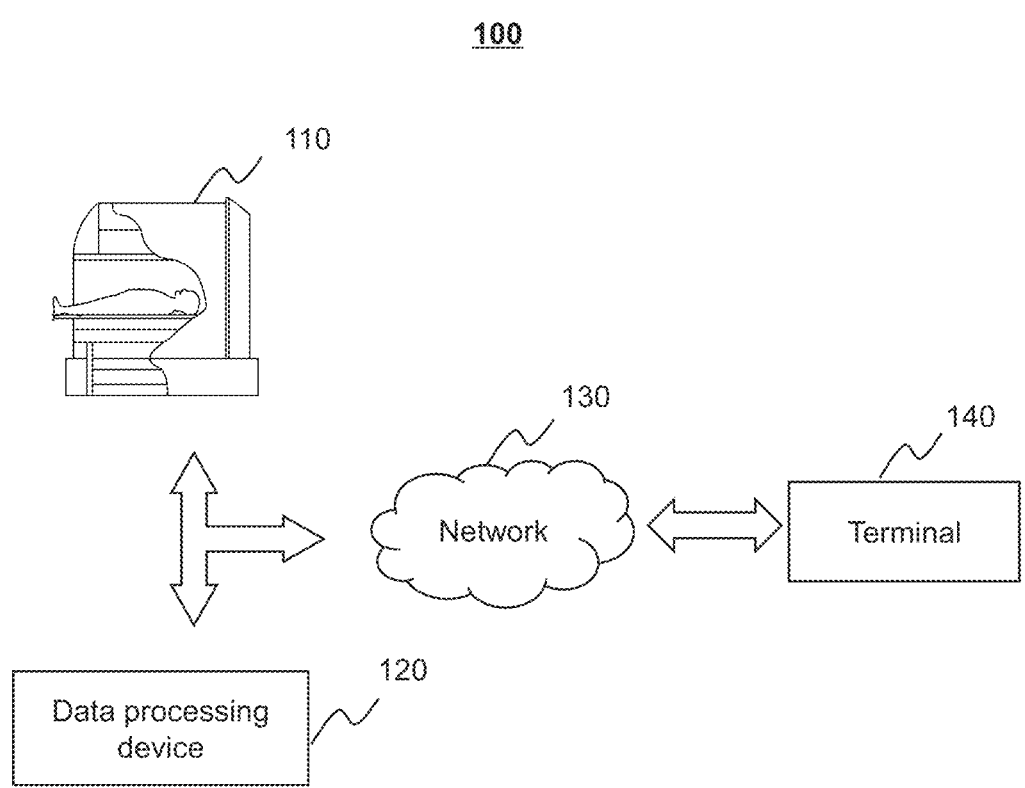
FIG. 1A is a schematic diagram illustrating an exemplary image processing system according to some embodiments of the present disclosure.

FIG. 1A is a schematic diagram illustrating an exemplary image processing system 100 according to some embodiments of the present disclosure. The image processing system 100 may include an imaging device 110, a data processing device 120, a network 130, and a terminal 140. In some embodiments, the imaging device 110, the data processing device 120, and the terminal 140 may be directly connected to each other. In some embodiments, the imaging device 110, the data processing device 120 and the terminal 140 may be indirectly connected to each other via the network 130. In some embodiments, the imaging device 110, the data processing device 120, and the terminal 140 may be indirectly connected to each other via one or more intermediate units (not shown). The intermediate unit(s) may be an entity (e.g., a device, an apparatus, a module, an interface, or the like, or a combination thereof), a non-entity (e.g., radio waves, optics, acoustic waves, electromagnetism, or the like, or a combination thereof), or the like, or a combination thereof. Different intermediate units may be connected wirelessly and/or wiredly.

The imaging device 110 may scan a target object and generate data (and/or image) related to the target object. The imaging device 110 may further process the image based on the data. In some embodiments, the target object may include a human body, an animal, or a part of the human body (or animal body), for example, an organ, a tissue, a lesion site (e.g., a tumor site), or any combination thereof. For example, the target object may be a head, a chest, an abdomen, a heart, a liver, an upper limb, a lower limb, a vertebra, a skeleton, a vessel, or the like, or any combination thereof. In some embodiments, the imaging device 110 may be a device or a group of devices. In some embodiments, the imaging device 110 may be a medical imaging device, such as, an MRI device, a SPECT device, a CT device, a PET device, or the like. In some embodiments, the medical imaging device(s) may be used alone and/or in combination. For example, the imaging devices used in combination may be a SPECT-MRI device, a CT-PET device, a SPECT-CT device, or the like. The imaging device 110 may include a scanner for scanning the target object, and obtain corresponding information (e.g., the image, the data, or the like). In some embodiments, the imaging device 110 may be a radioactive scan device. The radioactive scan device may include a radioactive scanning source for emitting radioactive rays to the target object. The radioactive rays may include corpuscular rays, photon rays, or the like, or a combination thereof. The corpuscular rays may include neutrons, protons, a-rays, electrons, p mediums, heavy ions, or the like, or a combination thereof. The photon rays may include X-rays, y-rays, ultraviolet rays, lasers, or the like, and a combination thereof. In some embodiments, the photon rays may be X-rays, and the corresponding imaging device 110 may be a CT system, a digital radiography (DR) system, a multi-modality imaging system, or the like, or a combination thereof. In some embodiments, the multi-modality imaging system may include a CT-PET system, a SPECT-MRI system, a SPECT-CT system, or the like, or a combination thereof. In some embodiments, the imaging device 110 may include a ray generation unit and a ray detection unit (not shown). For example, the imaging device 110 may include a photon detector configured for detecting the photon rays. The photon detector may trap the photons emitted from the target object. In some embodiments, the imaging device 110 may be a PET system ora multi-modality imaging system, of which the photon detector may include a scintillator and/or a photodetector. In some embodiments, the imaging device 110 may include a radio frequency transmitting coil and/or a radio frequency receiving coil (not shown). For example, the imaging device 110 may be an MRI imaging device.

The data processing device 120 may process information transmitted from the imaging device 110, the network 130, and/or the terminal 140. The information may include image information generated by the imaging device 110 or information relating to an object (e.g., a patient), information transmitted from a cloud device (not shown) via the network 130, a command and information issued by the terminal 140, or the like, or a combination thereof.

In some embodiments, the data processing device 120 may perform one or more operations relating to data processing, for example, querying, retrieving, reading and/or storage of the image data, execution of an image data processing algorithm, or the like, or a combination thereof. In some embodiments, the image data may include patient information and/or scan information, and the data processing device 120 may analyze the patient information and/or the scan information so as to determine a required processing algorithm. In some embodiments, the processing algorithm may include an image segmentation algorithm, an image splicing algorithm, an image registration algorithm, an algorithm for removing image background (e.g., an algorithm for removing a bed board, etc.), or the like, or a combination thereof. For example, the data processing device 120 may determine whether two images need to be spliced by analyzing the images. As another example, the data processing device 120 may analyze whether one or more specific organs, tissues, or sites (e.g., a vessel, a skeleton, etc.) in the image need to be segmented and/or removed. In some embodiments, the data processing device 120 may perform the processing algorithms for one or more two-dimensional/three-dimensional images based on an analysis result of the patient information and/or the scan information.

In some embodiments, the data processing device 120 may store and/or display a processing result. In some embodiments, the data processing device 120 may store and/or display the processing result at different times. For example, the data processing device 120 may store the processing result upon generating the processing result. As another example, the data processing device 120 may display the processing result as needed (e.g., when a user (e.g., a doctor) needs to view the image). In this way, when the user (e.g., a doctor) views the image, the processed image may be directly displayed, and the user may not need to wait for the execution of the image processing process, so as to save image-viewing time of the user.

Figure 2A:
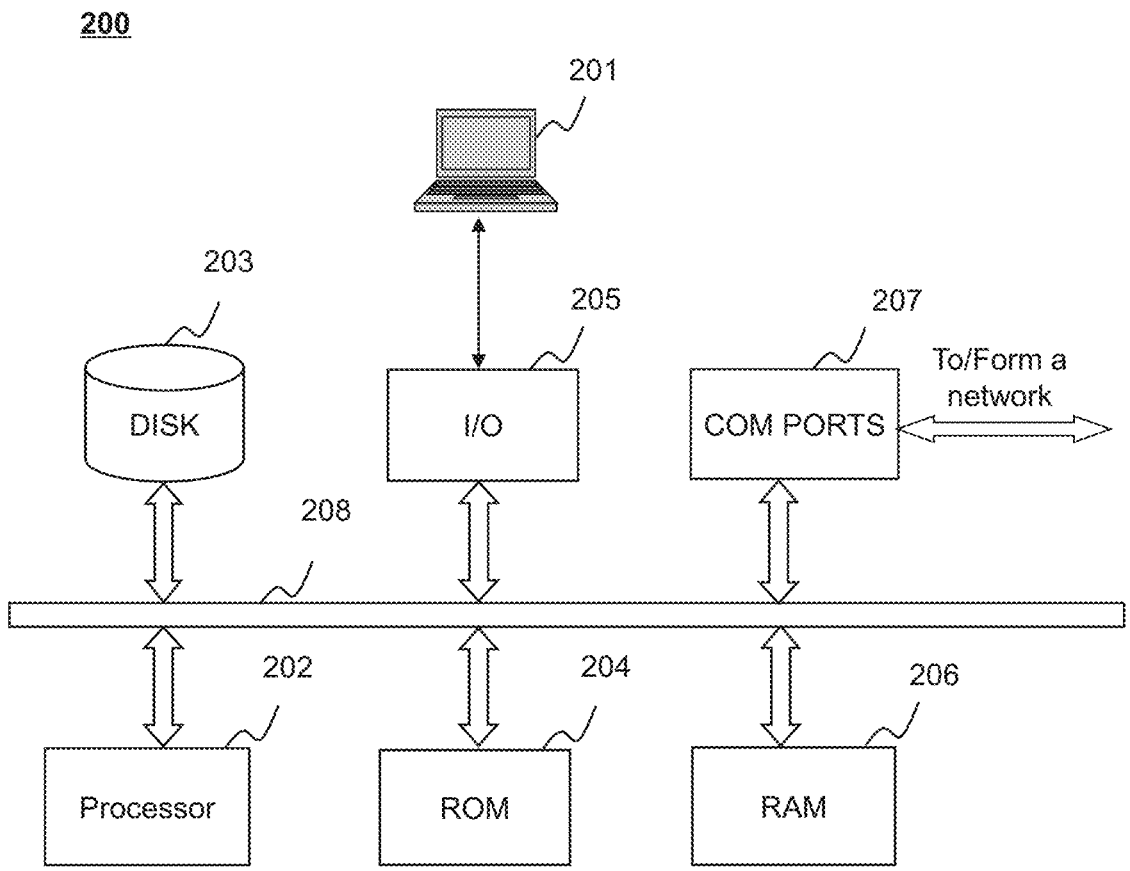
FIG. 2A is a schematic diagram illustrating exemplary hardware and/or software components of an exemplary computing device on which the image processing system may be implemented according to some embodiments of the present disclosure.

In some embodiments, one or more computing devices 200 having a hardware structure (see FIG. 2A) may implement the functions of the data processing device 120. FIG. 2A shows a schematic diagram illustrating exemplary hardware and/or software components of an exemplary computing device on which the image processing system may be implemented according to some embodiments of the present disclosure.

The network 130 may be a single network or a combination of multiple networks. For example, the network 130 may be a local area network (LAN), a wide area network (WAN), a public switched telephone Network (PSTN), a virtual network (VN), a private network (PN), a metropolitan area network (MAN) or a combination thereof. The network 130 may include a plurality of network access points, and may use a wired network framework, a wireless network framework, and a hybrid framework of wired/wireless networks. The wired network may use a combination of one or more cables, for example, a metal cable, a hybrid cable, an optical fiber cable, or the like. The wireless network may include blue tooth, Wi-Fi, ZigBee, near field communication (NFC), a cellular network (e.g., GSM, CDMA, 3G, 4G, etc.), or the like, or a combination thereof. The description of the network 130 is merely provided for the purposes of illustration, and not intended to limit the scope of the present disclosure.

Figure 2B:
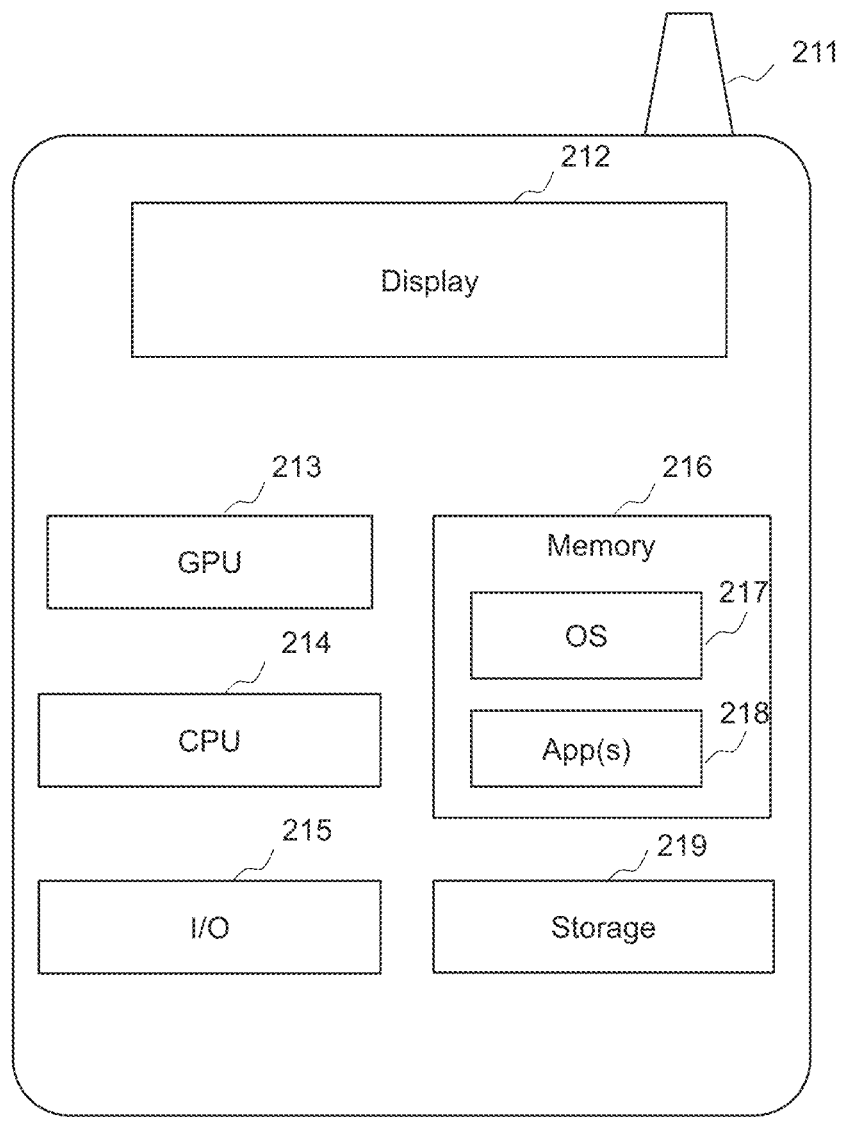
FIG. 2B is a schematic diagram illustrating exemplary hardware and/or software components of an exemplary mobile device on which the terminal may be implemented according to some embodiments of the present disclosure.

The terminal 140 may receive, process, store, and/or display image data. In some embodiments, the terminal 140 may transmit information to the imaging device 110 and/or the data processing device 120 via the network 130. In some embodiments, the terminal 140 may be used by one or more users, for example, medical care worker in a hospital, a medical college and/or a student thereof, a non-medical care worker that has been trained, or the like, or a combination thereof. In some embodiments, the terminal 140 may be a terminal device (e.g., a display screen, a printer, a computing device, or the like, or a combination thereof) connected to the imaging device 110, the data processing device 120, and/or the network 130. In some embodiments, the terminal 140 may the computing device 200 with the hardware structure (see FIG. 2A) or a mobile device 210 (see FIG. 2B). FIG. 2B shows a schematic diagram illustrating exemplary hardware and/or software components of an exemplary mobile device on which the terminal may be implemented according to some embodiments of the present disclosure.

It should be noted that the description of the data processing device 120 is merely provided for illustration purposes, and not intended to limit the scope of the present disclosure. For persons having ordinary skills in the art, multiple variations and modifications may be made under the teachings of the present disclosure. However, those variations and modifications do not depart from the scope of the present disclosure. For example, the system may include two or more imaging devices 110. As another example, the system may have two or more terminals 140.

Figure 1B:
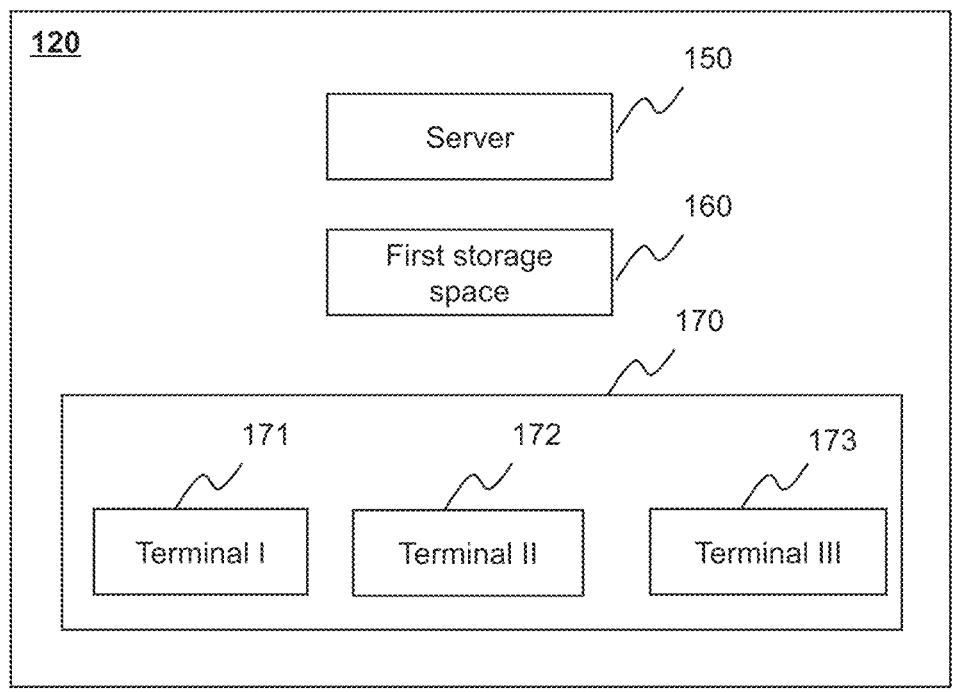
FIG. 1B is a schematic diagram illustrating an exemplary data processing device according to some embodiments of the present disclosure.

FIG. 1B is a schematic diagram illustrating an exemplary data processing device 120 according to some embodiments of the present disclosure. A data processing device 120 may include a server 150, a first storage space 160, and one or more terminals 170. In some embodiments, the first storage space 160 may be in an internal memory of the server 150. In some embodiments, the first storage space 160 may be independent of the server 150. In some embodiments, the first storage space may refer to a storage space including a first storage location. In some embodiments, the server 150 may access the first storage space by searching the first storage location. For example, the server 150 may query and/or locate the first storage location, and store information starting from the first storage location. The number of the terminals 170 may be equal to or larger than 1 (see, e.g., a terminal I 171, a terminal II 172, a terminal III 173, or the like), In some embodiments, the server 150, the first storage space 160, and/or the terminal(s) 170 may be directly and/or indirectly connected to each other (e.g., via the network 130). In some embodiments, the server 150, the first storage space 160, and the terminal(s) 170 may be indirectly connected to each other via one or more intermediate units (not shown). The intermediate unit may be an entity (e.g., a device, an apparatus, a module, an interface, or the like, or a combination thereof), a non-entity (e.g., radio waves, optics, acoustic waves, electromagnetism, or the like, or a combination thereof), or the like, or a combination thereof. The intermediate units may be connected wirelessly and/or wiredly.

The server 150 may process the image data and/or obtain the processing result. Before processing the data, the server 150 may acquire the data corresponding to at least one image. In some embodiments, the server 150 may acquire an image type (or a type of the image data). The image type may be determined based on information about the scan regions of the object presented in the image and/or the scan mode. In some embodiments, the server 150 may not need to preset and/or modify the image type. The image may be a medical image. In some embodiments, the image type may refer to the type of the information (or an object) or the content displayed in the image. The image type may include a head image, a chest image, a hand image, a hip image, a leg image, a foot image, or the like, or a combination thereof. In some embodiments, the image type may be acquired by the server 150 in various ways. For example, the server 150 may acquire identification information in the image after receiving the image, and acquire the image type based on the identification information. As another example, after receiving the image, the server 150 may compare image feature of the image and various types of standard images, acquire similarity between the image and the standard images, and designate the type corresponding to the standard image having the maximum similarity as the image type.

The server 150 may process images with various image types based on one or more data processing algorithms. In some embodiments, image(s) with an image type may be processed based on one or more corresponding data processing algorithms. The correspondence between the image type(s) and the data processing algorithm(s) may be stored in the server 150 in advance. After determining the image type, the server 150 may determine one or more data processing algorithms to be used based on the correspondence. For example, the corresponding data processing algorithm for the medical image may include one or more of bed board removing, vessel segmentation, organ segmentation, colon segmentation, splicing, lung nodule segmentation, perfusion, etc. As another example, the corresponding data processing algorithm for the head image may include various data processing algorithms (e.g., ten algorithms), for example, a registration algorithm, a bone removing algorithm, a bed board removing algorithm, etc. In some embodiments, upon the image type being determined as a head image, the server 150 may determine the data processing algorithms (e.g., ten data processing algorithms including the registration algorithm, the bone removing algorithm, the bed board removing algorithm, etc.) to be used for processing the head image. In some embodiments, upon determining the data processing algorithm corresponding to the image type, the server 150 may use the data processing algorithm to process the image.

In some embodiments, the server 150 may store the processing result in the first storage space 160. The terminal 170 may access, read, and/or edit the data processing result stored in the first storage space 160. In some embodiments, the first storage space 160 may be preset according to one or more practical needs. For example, the first storage space 160 may be deployed in a local-cache of the server 150 (e.g., a storage space independently developed in the local-cache of the server 150). As another example, the first storage space 160 may be arranged in an offline or online storage device of the data processing device 120. In some embodiments, the server 150 may be an integrated standalone device connected to the network, or may include a plurality of components connected to the network in a distributed manner. In some embodiments, the terminal 170 may be a terminal integrating with one or more application programs, one or more service components (e.g., a mobile phone, a tablet, a desktop, or the like). In some embodiments, the communication between the server 150 and the terminal(s) 170 may be directly realized based on one or more self-defined communication standards or one or more industry general communication standards (e.g., TCP protocol, UDP protocol, etc.). It should be noted that the above description of the communication standards is merely provided for the purposes of illustration, and not intended to limit the scope of the present disclosure.

In some embodiments, the data processing device 120 may include two or more terminals 170. In some embodiments, each terminal 170 may perform a same data processing on a same image. For example, if the disease state (e.g., a brain disease) of a patient involves a plurality of departments of a hospital, it may be possible that the terminals 170 of different departments share a same brain CT image of the same patient. The server 150 may store obtained processing results in the first storage space 160, such that one or more terminals 170 may separately obtain the processing results from the first storage space 160.

FIG. 2A is a schematic diagram illustrating exemplary hardware and/or software components of an exemplary computing device on which the image processing system may be implemented according to some embodiments of the present disclosure. The computing device 200 may realize and/or implement a particular system (e.g., the data processing device 120) disclosed in the present disclosure. A functional block diagram may be used to explain a hardware platform including a user interface of the system in the present disclosure. The computing device 200 may implement one or more components, modules, units, sub-units of the data processing device 120. The computing device 200 may be a general-purpose computer or a special-purpose computer. For brevity, only one computing device is displayed in FIG. 2A. Computing function of the required information relating to data processing may be provided by a set of similar platforms in a distributed manner according to this disclosure, so as to disperse processing loads of the system.

As shown in FIG. 2A, the computing device 200 may include a user interface 201, an internal communication bus 208, a processor 202, a hard disk 203, a read only memory (ROM) 204, an input/output component 205, a random access memory (RAM) 206, and a communication port 207. The internal communication bus 208 may implement data communication among the components of the computing device 200. The processor 202 may execute a program instruction, and/or complete any function, component, module, unit, and sub-unit of the image processing system 100 described in the present disclosure. The instruction may indicate which one of a plurality of images received by the server 150 is to be processed. The processor 202 may include one or more processors. In some embodiments, the processor 202 may include a microcontroller, a reduced instruction set computer (RISC), an application specific integrated circuit (ASIC), an application-specific instruction-set processor (ASIP), a central processing unit (CPU), a graphics processing unit (GPU), a physics processing unit (PPU), a microprocessor unit, a digital signal processor (DSP), a field programmable gate array (FPGA), or the other circuits or processors capable of executing the computer program instruction, or the like, or a combination thereof.

In some embodiments, the processor 202 may control the imaging device 110, the data processing device 120, and/or the terminal 140. In some embodiments, the processor 202 may control the imaging device 110, the data processing device 120, and the terminal 140 to receive information, or send information to the above system(s) and/or device(s). In some embodiments, the processor 202 may receive image information or information relating to the target object from the imaging device 110. The processor 202 may send the image information or the information relating to the target object to the data processing device 120. The processor 202 may receive processed data or image from the data processing device 120. The processor 202 may send the processed data or image to the terminal 140. In some embodiments, the processor 202 may execute programs, algorithms, software, or the like. In some embodiments, the processor 202 may include one or more interfaces. The interface(s) may include an interface between the imaging device 110, the data processing device 120, the terminal 140 and/or the other modules or units of the image processing system 100.

In some embodiments, the processor 202 may execute a command obtained from the terminal 140. The processor 202 may control imaging device 110 and/or data processing device 120 by processing and/or converting the command. For example, the processor 202 may process user input information by the terminal 140, and convert the information to one or more corresponding commands. The command may be scan time, location information of the target object, a rotation speed of a gantry of the imaging device 110, a scan parameter, a data processing parameter, or the like, or a combination thereof. The processor 202 may control the data processing device 120 to select different algorithms, so as to process and/or analyze the image data. In some embodiments, the processor 202 may be integrated in an external computing device which is used for controlling the imaging device 110, the data processing device 120, and/or the terminal 140, or the like. In some embodiments, the processor 202 may include one or more nodes. Each node may execute a process. A node may be a single chip microcomputer or an independent computer, or may be one of a plurality of virtual nodes of a computer.

In some embodiments, the computing device 200 may include one or more storage devices in one or more forms (e.g., the hard disk 203, the read only memory (ROM) 204, the random access memory (RAM) 206, a cloud memory (not shown)) used for storing data, programs, and/or algorithms, or the like. The storage device may store various data files used in the processing process and/or communication, and/or program instructions executed by the processor 202. The storage device may be located inside or outside of the image processing system 100 (e.g., external storage devices, the cloud memory, or the like, connected via the network 130). The storage device (e.g., the hard disk 203, the read only memory (ROM) 204, the random access memory (RAM) 206, the cloud memory (not shown)) may store the information obtained from the imaging device 110, the data processing device 120, and/or the terminal 140. The information may include image information, programs, software, algorithms, data, texts, numbers, images, audios, etc, that may be used in the data processing process, or the like, or a combination thereof.

The hard disk 203 may be a device which stores information using magnetic energy. In some embodiments, the hard disk 203 may be a floppy disk, a magnetic tape, a magnetic core memory, a bubble memory, a USB flash disk, a flash memory, etc. which stores information using the magnetic energy. The read only memory (ROM) 204, and/or the random access memory (RAM) 206 may store information using electric energy. The read only memory (ROM) 204 may include an optical disc drive, a hard disk, a magnetic tape, a non-volatile random access memory (NVRAM), a non-volatile SRAM, a flash memory, an electrically-erasable programmable read-only memory, an erasable programmable read-only memory, programmable read-only memory, or the like, or a combination thereof. The random access memory (RAM) 206 may include a dynamic random access memory (DRAM), a static random access memory (SRAM), a thyristor random access memory (T-RAM), a zero-capacitor random access memory (Z-RAM), or the like, and a combination thereof.

In some embodiments, the storage device may be a device that stores information in an optical way, such as CD, DVD, etc. In some embodiments, the storage device may be a device that stores the information in a magneto-optic way, such as a magneto optical disk. An access mode of the storage device may include random storage, series access storage, read-only storage, or the like, or a combination thereof. The above storage device may be a non-permanent memory storage device, or a permanent memory storage device. It should be noted that the above description of the above storage device is merely provided for the purposes of illustration, and not intended to limit the scope of the present disclosure. The above storage devices may be local or remote. The above storage devices may be centralized or distributed. For example, the above storage devices may be located in a cloud server (not shown).

The input/output component (also referred to as I/O) 205 may support the input and/or output (e.g., receiving, sending, displaying, printing of information, etc.) of data stream(s) between the computing device 200 and one or more components of the image processing system 100 (e.g., the imaging device 110, the terminal 140, or the like). In some embodiments, the input/output component 205 may include a keyboard, a touch device, a mouse, a mechanical analogy device, a wearable device (e.g., a three-dimensional glass, a mechanical glove, or the like), a virtual reality device, an audio input device, an image input device, a remote control device, or the like, or a combination thereof. The output information may be sent or may not be sent to the user. The output information that is not sent may be stored in the hard disk 203, the read only memory (ROM) 204, the random access memory (RAM) 206, or may be deleted. In some embodiments, the user may input some original parameters or set an initialization condition corresponding to the data processing by the input/output component 205. In some embodiments, information may be input from an external data source (e.g., the floppy disk, the hard disk, a compact disk, a memory chip, a wired terminal, a wireless terminal, or the like, or a combination thereof). The input/output component 205 may receive information from another module or unit of the image processing system 100, or may send information to another module or unit of the system.

The communication port 207 may implement the data communication between the computing device 200 and one or more parts of the image processing system 100 (e.g., the imaging device 110, the terminal 140, or the like). The computer may send and/or receive the information (and/or data) from the network 130 by the communication port 207. The form of the information output by the image processing system 100 may include a number, a character, an instruction, a sound, an image, a system, software, a program, or the like, or a combination thereof.

The user interface 201 may display information generated during the data processing process, or the data processing result (e.g., an image splicing result, an image segmentation result, or the like, or a combination thereof). The user interface 201 may implement interaction between the user and the data processing process, for example, a control of the starting or stopping of the processing process by the user, the selecting or modifying of an operational parameter, the selecting or modifying of an algorithm, the modifying of a program, the exiting of the system, the maintaining of the system, the upgrading of the system, the system updating, or the like.

It should be noted that the storage device (the hard disk 203, the read only memory (ROM) 204, the random access memory (RAM) 206, a cloud memory, or the like) and/or the processor 202 may actually exist in the system. In some embodiments, the corresponding functions of the storage device and/or the processor 202 may be implemented by a cloud computing platform. The cloud computing platform may include a storage-type cloud platform for storing data, a computing-type cloud platform for processing data, and a synthetic cloud platform for the data storage and processing. The cloud platform used by the image processing system 100 may be a public cloud, a private cloud, a community cloud, a hybrid cloud, or the like. For example, according to the practical needs, a portion of the information received by the image processing system 100 may be processed and/or stored by the cloud platform, while the other portion(s) of the information may be processed and/or stored by a local processing device and/or storage device.

In some embodiments, the image processing system 100 may have one or more computing devices 200. The plurality of computing device 200 may realize and/or implement the same or different functions. For example, a first computing device may control the imaging device 110 to image, and obtain the image data. As another example, a second computing device may acquire the image data from the first computing device or a storage device, process the image data, and store the processing result. As a further example, a third computing device may acquire the processing result from the second computing device, display the result in a visualization manner so as to display it when the user (e.g., the doctor) views the image.

FIG. 2B is a schematic diagram illustrating exemplary hardware and/or software components of an exemplary mobile device on which the terminal may be implemented according to some embodiments of the present disclosure. The mobile device 210 may realize and/or implement a particular system disclosed in the present disclosure. In some embodiments, the terminal 140 may be a mobile device 210 for displaying information relating to user interaction. The mobile device 210 may have various forms, including a smartphone, a tablet, a music player, a portable game console, a global positioning system (GPS) receiver, a wearable computing device (e.g. glasses, a watch), or the like, or any combination thereof. In some embodiments, the mobile device 210 may include one or more antennae 211 (e.g., a wireless communication unit), a display module 212, a graphics processing unit (GPU) 213, a central processing unit (CPU) 214, an input/output module 215, a memory 216, and a storage 219. Although the antenna 211 in FIG. 2B is displayed outside the mobile device 210, the antenna 211 may also be provided within the mobile device 210. In some embodiments, the mobile device 210 may also include any other suitable component, such as a system bus controller (not shown). As shown in FIG. 2B, a mobile operating system 217 (such as iOS, Android, Windows Phone, etc.), and/or one or more applications 218 may be loaded from the storage 219 into the memory 216 and executed by the central processing unit (CPU) 214. The applications 218 may include a browser and/or other mobile application suitable for receiving and/or processing information relating to the image on the mobile device 210. The input/output module 215 may provide an interactive function of information relating to the image data. The input/output module 215 may implement interaction of information between the mobile device 210 and the data processing device 120, and/or other components of the image processing system 100, for example, transmit information via the network 130.

In order to implement different modules, units as well as functions thereof as described above, the computing device 200 and/or the mobile device 210 may act as a hardware platform of one or more components described above (e.g., the data processing device 120, the terminal 140, and/or other components of the image processing system 100 described in FIG. 1). Hardware elements, operating systems, and programming languages of such computers are common in nature and it may be assumed that those skilled in the art will be sufficiently familiar with these techniques and will be able to use the techniques described herein to provide the information required for data processing. A computer that contains user interface elements can be used as a personal computer (PC) or other type of a workstation or a terminal device, and can be used as a server after being properly programmed. It may be understood that those skilled in the art will be familiar with such structures, programs, as well as general operations of such computer equipment, and therefore all accompanying drawings do not require additional explanation.

Figure 3:
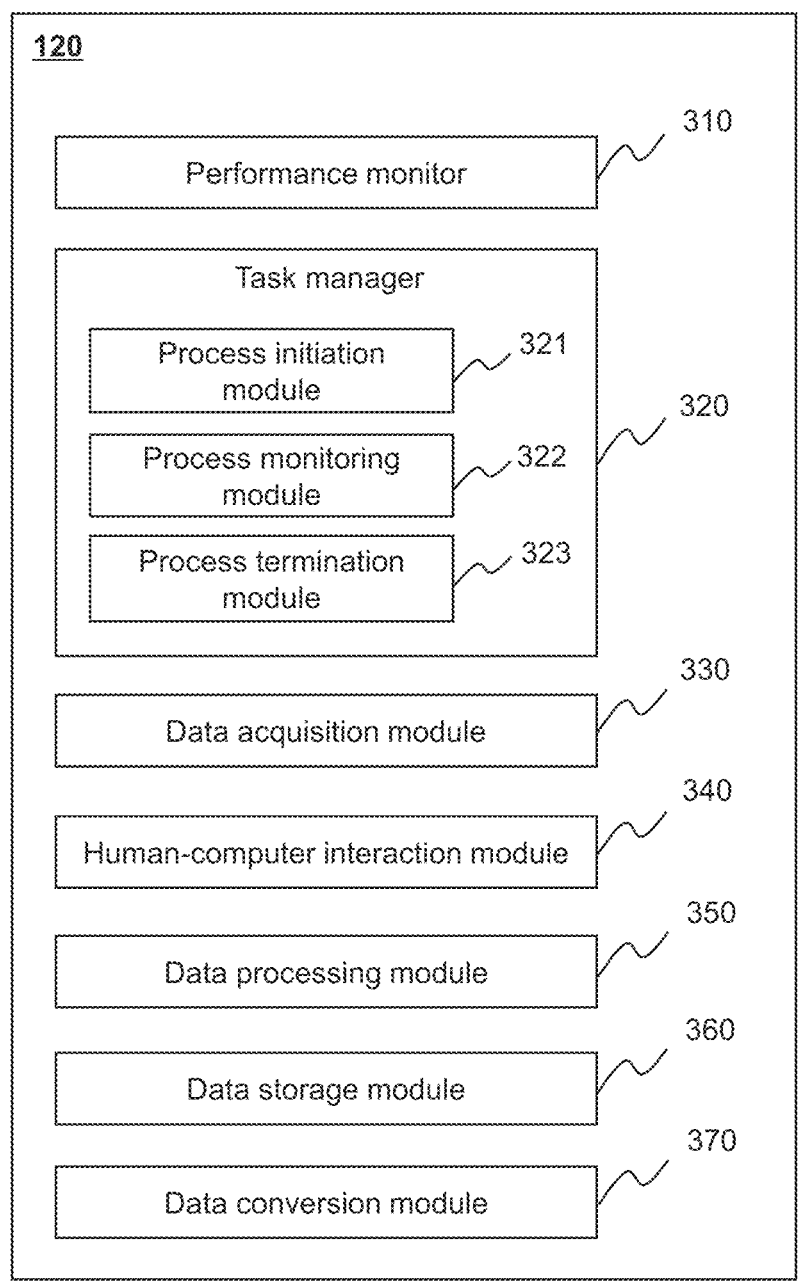
FIG. 3 is a schematic diagram illustrating an exemplary data processing device according to some embodiments of the present disclosure.

FIG. 3 is a schematic diagram illustrating an exemplary data processing device 120 according to some embodiments of the present disclosure. The data processing device 120 may include a performance monitor 310, a task manager 320, a data acquisition module 330, a human-computer interaction module 340, a data processing module 350, a data storage module 360, and a data conversion module 370. It should be noted that the data processing device 120 illustrated in FIG. 3 is merely representative of some embodiments of the present disclosure, and those skilled in the art will be able to make modifications, additions, and subtractions in accordance with the description of the data processing device 120 without paying creative effort. For example, two modules thereof may be combined into one module. As another example, one module thereof may be segmented into two or more modules.

The performance monitor 310 may monitor the server 150. For example, the performance monitor 310 may monitor running state information of the server 150, a load of the processor 202 or the central processing unit (CPU) 214, a usage rate of a memory (e.g., a read-only memory (ROM) 204, the random access memory (RAM) 206, the memory 216, etc.), a usage rate of a hard disk (e.g., the hard disk 203), or the like, or any combination thereof. In some embodiments, the performance monitor 310 may implement remote monitoring based on remote data interchange or implement local monitoring by analyzing locally collected data. In some embodiments, the performance monitor 310 may monitor a system load of the current system including an overall memory usage rate of the system, an overall CPU occupancy rate of the system, an overall disk utilization of the system, whether storage medium works normally, network speed, machine failure, or the like. In some embodiments, information monitored by the performance monitor 310 may be shown by the user interface 201 and/or the display module 212.

In some embodiments, the performance monitor 310 may check the system load in real time or at a regular time interval. In some embodiments, if the performance monitor 310 monitors that the system load is excessively heavy, the performance monitor 310 may notice the server 150 or the terminal 140 to terminate one or more running processes so as to alleviate the current load of the system. In some embodiments, that the system load is excessively heavy may refer that the memory usage rate, the CPU occupancy rate, the hard disk usage rate, or the like exceeds one or more preset thresholds (e.g., 50%, 60%, 70%, 80%, 90%, or the like). In some embodiments, if the performance monitor 310 has monitored some abnormal situations (e.g., a storage medium is unable to read or store data, there is no network speed, there is a machine failure, etc.), the performance monitor 310 may notice the server 150 or the terminal 140, so that the server 150 or the terminal 140 may take corresponding measure(s). For example, if the storage medium is damaged, the performance monitor 310 may monitor that a node state of the damaged storage medium is unavailable, and the server 150 may not be able to access resources stored in the node.

The task manager 320 may detect information relating to one or more running processes in the server 150, and/or manage the running process(es) in the server 150. In some embodiments, information detected by the task manager 320 may be shown by the user interface 201 and/or the display module 212. A user may check information via the user interface 201 and/or the display module 212, such as a number of processes currently executed by the server 150, names of the processes, memory usage rates of one or more processes, CPU occupancy rates of one or more processes, hard disk space usage rates of one or more processes, etc. The task manager 320 may manage and/or operate the processes. For example, the task manager 320 may schedule the processes, allocate the processes, initiate the processes, monitor the processes, terminate the processes, or the like. The task manager 320 may plan resources of the server 150 and allocate the resources to one or more processes for use. For example, the task manager 320 may notice one or more nodes to initiate a process, and determine whether a node successfully initiates a process, so that a running node may be prevented from being allocated too many processes or a node in a failure state may be prevented from initiating a process, and corresponding affection on the operating efficiency of the process(es) may be avoided. A node may be a single chip microcomputer or an independent computer in the server 150, or may be one of a plurality of virtual nodes of a computer. If a node cannot initiate a process, the task manager 320 may exclude the node, and determine another node in the remaining nodes to initiate the process. If the process is initiated successfully, the task manager 320 may feedback registration information of the node (e.g., a network address, etc.) to the server 150. A node resource table may be generated in this way. In some embodiments, the task manager 320 may feedback process information, and/or update the node resource table, so that the server 150 may effectively schedule other nodes to complete an additional process task. In some embodiments, information fed back by the task manager 320 may be shown by the user interface 201 and/or the display module 212. In some embodiments, the task manager 320 may include a process initiation module 321, a process monitoring module 322, and a process termination module 323.

The process may be one or more running activities of one or more programs. The program(s) may have one or more independent functions. The process may perform operations and/or processing on one or more data sets. The process may include code(s) corresponding to a program and/or a currently running program. A process may be a basic unit for performing resource allocation and scheduling by the system. In some embodiments, the process may be a running program. The program may be a static entity. For example, the program may have corresponding code(s). The code(s) may be stored statically in the server 150 when not being executed. If the processor 202 execute the code(s), the program may be run, and a corresponding function may be executed. An executing program can be regarded as a process. In some embodiments, two or more processes may be executed independently, which may indicate that the operational activities, the data utilized, and/or the data generated thereof may not affect each other. For example, two or more processes can perform different operations on a same data set. As another example, two or more processes can perform the same operations on two or more different data sets.

In some embodiments, a process may execute one or more processing functions, or a part of a processing function. For example, a process may execute an operation for removing a bed board on a medical image. As another example, a process may execute an operation for removing a bone on a medical image. As a further example, a process may execute the extraction of a vessel centerline, and the extraction of the vessel centerline may be an intermediate operation of vessel segmentation.

The process initiation module 321 may initiate one or more processes. In some embodiments, the process initiation module 321 may be configured on the computing device 200, or the terminal 140, or the like. In some embodiments, the process initiation module 321 may receive process initiation instructions from the terminal 140, the processor 202, the input/output component 205, or the like. In some embodiments, the process initiation instructions may be directly triggered by a user. For example, the user may input a process initiation instruction via the user interface 201. In some embodiments, the process initiation instruction may be generated by the server 150 analyzing related information and/or executing related instructions, or the like. For example, the process initiation module 321 may automatically initiate a process of a corresponding program based on related information of a patient. The related information of the patient may include clinic indications, laboratory data, previous imaging report(s), other report(s) generated from clinic examinations, or the like. For example, the process initiation module 321 may automatically initiate a vessel segmentation process based on angiographic data of the patient obtained by the server 150.

In some embodiments, the server 150 may receive registration information of the node(s) (e.g., a network address, etc.) and/or form a node resource table. The process initiation module 321 may determine whether computational resources required by a process exceed a load threshold of each candidate node, so as to prevent a running node from being allocated too many processes or to prevent a node in a failure state from initiating a process, and thus the efficiency of the process may not be affected. The process initiation module 321 may notice a node to initiate a process, and determine whether the node has initiated the process successfully. If the node cannot initiate the process, then the node may be excluded, and the process initiation module 321 may determine another node in the remaining candidate nodes to initiate the process. If the process is initiated successfully, the process initiation module 321 may feedback registration information of the node (e.g., a network address, etc.) to the server 150, and/or may form the node resource table. In some embodiments, the process initiation module 321 may feedback process information to the server 150, and/or update the node resource table, so that the server 150 may effectively schedule other nodes to complete an additional process task. In some embodiments, the information fed back by the process initiation module 321 may be shown by the user interface 201 and/or the display module 212.

The process monitoring module 322 may monitor the running states of one or more processes. In some embodiments, the process monitoring module 322 may check a number of processes currently executed by the server 150, a memory usage rate of each process, a CPU occupancy rate of each process, a hard disk usage of each process, an execution condition of each process (e.g., a completion rate of the process, the execution time of the process, the remaining time for the execution of the process, whether the process runs normally, etc.) in real time or at a certain time interval.

In some embodiments, the process monitoring module 322 may monitor whether execution conditions of the process(es) are abnormal, for example, whether a process is interrupted or whether the process terminates abnormally. In some embodiments, the process monitoring module 322 may set a corresponding time threshold T for one or more currently running processes. If the execution time of a process exceeds the time threshold T, and a node does not complete the process, then the process monitoring module 322 may trigger a response. The response may include that the process monitoring module 322 notifies the node to close the process. Further, the process monitoring module 322 may exclude the node and allocate the uncompleted process to another node among the candidate nodes, so that the execution of the uncompleted process may be continued. In some embodiments, the process monitoring module 322 may collect load information, resource information, and state information of each node, so as to monitor the state of the process(es) executed by each node in real time. If a failure occurs in a certain node (e.g., a process of the node runs abnormally), the task manager 320 may schedule the process executed by the failure node to another node so that the execution of the process may be continued, thereby ensuring that the process is not interrupted or reset due to node failure. The task manager 320 may monitor and/or schedule a load of each node in real time, optimize resources of each node, and improve the execution speed of the process(es). In some embodiments, the response may include that the process monitoring module 322 notifies the process termination module 323 to terminate the process.

The process termination module 323 may terminate a running process. The process termination module 323 may be configured on the computing device 200, or the terminal 140, or the like. In some embodiments, the process termination module 323 may receive process termination instructions from the terminal 140, the processor 202, the input/output component 205, or the like. In some embodiments, the process termination instructions may be directly triggered by a user. For example, the user may input the process termination instructions via the user interface 201. In some embodiments, if the process monitoring module 322 monitors that a memory usage rate exceeds a certain threshold (e.g., 50%, 60%, 70%, 80%, 90%, etc.), then the process monitoring module 322 may trigger a response. The response may include that the process termination module 323 terminates or interrupts the running process. In some embodiments, if the process monitoring module 322 monitors that a failure occurs in a certain node, the process termination module 323 may terminate the process executed in the failure node.

The data acquisition module 330 may acquire image data and/or an image. The image data and/or the image may be acquired from the imaging device 110, the terminal 140, a local data source, such as a storage device (e.g., the hard disk 203, the read-only memory (ROM) 204, the random access memory (RAM) 206, etc.), the input/output component 205, or an external data source (e.g., a cloud memory, etc.) via the network 130.

The target object associated with the acquired image and/or data may be a human body, an animal, or a part thereof, for example, an organ, a tissue, a lesion site (e.g., a tumor site), or any combination thereof. For example, the target object may be a head, a chest, a heart, a liver, an upper limb, a lower limb, a vertebra, a skeleton, a vessel, or the like, or any combination thereof. In some embodiments, the acquired image data may be three-dimensional image data and/or two-dimensional image data. In some embodiments, the acquired image data may be image data generated at various times, by various imaging devices, and/or under various conditions (e.g., at various illuminations, at various scan positions, at various angles, etc.). In some embodiments, the acquired image data may be image data of a single modality and/or image data of a plurality of modalities. For example, the image data may be an MRI image, a CT image, a PET image, a SPECT-MR image, a CT-PET image, a CE-SPECT image, a DSA-MR image, a PET-MR image, a FET-US image, a SPECT-US image, an US-CT image, an US-MR image, or the like, or a combination thereof. In some embodiments, the acquired image data may be associated with one or more specific scan regions based on one or more examination requirements. For example, the acquired image data may include information of full scanning of the target object, information of a blood vessel, information relating to a nerve distribution, information relating to a functional area of the target object, information relating to a tissue metabolism, or the like, or a combination thereof. In some embodiments, the acquired image data may include data of the target object and/or data of examination background, for example, data corresponding to an examination bed board.

In some embodiments, the data acquisition module 330 may automatically acquire the image data based on a processing instruction received by the human-computer interaction module 340. For example, if the instruction received by the human-computer interaction module 340 indicates processing of a lung image, the data acquisition module 330 may automatically acquire a corresponding lung image based on the instruction. As another example, if the instruction received by the human-computer interaction module 340 indicates processing of a cerebral perfusion image, the data acquisition module 330 may automatically acquire a corresponding cerebral perfusion image based on the instruction.

The human-computer interaction module 340 may implement information communication between a user and a device. In some embodiments, the human-computer interaction module 340 may show intermediate information and/or a result of data processing to the user. In some embodiments, the user may, by the human-computer interaction module 340, set or modify parameters used in data processing, modify a flow or an algorithm used in data processing, or artificially intervene a data processing process (e.g., input a command to initiate the process, forcibly quit or terminate the process, etc.). In some embodiments, the human-computer interaction module 340 may implement functions by the input/output component 205. Further, the human-computer interaction module 340 may include a visualization display device, a user interface which can be operated by the user, an extension interface, or the like, or a combination thereof. The user interface may allow the user to control and execute an operation instruction. For example, the user may input an operation command or operation parameters using the input/output component 205 (e.g., a touch screen, a microphone, a keyboard, a mouse, a joystick, a touch pad, a touch pen, a voice recognition apparatus, a gesture recognition apparatus, etc.), so as to implement information interaction between the user and the device. In some embodiments, the human-computer interaction module 340 may display a medical image, a task manager scheduler program, a process running state, or the like.

In some embodiments, the user may input one or more processing instructions by the human-computer interaction module 340. In some embodiments, the processing instruction may indicate an operation including, for example, an adjustment of a window width and/or a window level, image zooming, image measuring and/or annotating, management of data relating to a patient, two-dimensional and/or three-dimensional image processing, reconstruction of a medical image using a three-dimensional volume technique, three-dimensional view adjustment and/or color adjustment, automatic editing and/or volume measurement based on a target region of an image, or the like. In some embodiments, the processing instruction may relate to a medical image, a thumbnail, or a detection number, or the like. The thumbnail may be a compressed medical image with a reduced resolution. The detection number may correspond to a medical image scanning at a certain time or of a batch.

The data processing module 350 may perform processing on the acquired image data. In some embodiments, the data processing module 350 may determine a processing function required to be implemented. The data processing module 350 may determine the processing function required to be implemented based on the image data acquired by the data acquisition module 330 or the processing instruction received by the human-computer interaction module 340. For example, the data processing module 350 may analyze a scan region and/or an imaging modality thereof based on the medical image or the thumbnail received by the human-computer interaction module 340, and may then analyze a processing algorithm required to be executed for an image including the scan region. As another example, the data processing module 350 may acquire image data of one or more images corresponding to the detection number based on the detection number received by the human-computer interaction module 340, and then analyze a processing algorithm required to be executed for the image data. In some embodiments, the data processing module 350 may execute a corresponding processing operation based on the determined processing function. For example, the data processing module 350 may infer a processing function required to be performed for the image data acquired by the data acquisition module 330 when a user views the image, and perform one or more corresponding processing operations before the user views the image. As another example, the data processing module 350 may perform one or more processing operations (e.g., registration, removing a bone, removing a bed board, or the like, or a combination thereof) on an acquired cerebral perfusion image. As a further example, the data processing module 350 may perform one or more processing operations (e.g., removing a bone, vessel segmentation, or the like, or a combination thereof) on an acquired vessel CT image. As a further example, the data processing module 350 may perform one or more processing operations (e.g., lung segmentation, trachea extraction, rib segmentation, vertebra segmentation, sternum segmentation, or the like, or a combination thereof) on an acquired chest CT image. In some embodiments, the data processing module 350 may perform one or more processing required operations related to the image data.

The data storage module 360 may store a processing result generated by the data processing module 350. The processing result may include one or more processed images. In some embodiments, the data storage module 360 may automatically store the processing result. In some embodiments, the data storage module 360 may store the process result based on the instruction received by the human-computer interaction module 340. The data storage module 360 may store the processing result in one or more formats. The format(s) may include a joint photographic experts group (JPEG), a portable network graphics (PNG), a bitmap file (Bitmap), BMP, AVI, a portable document format (PDF), a tagged image file format (TIFF), a waveform audio file format(WAV), digital imaging and communications in medicine (DICOM), a moving picture experts group (MPEG), or the like. In some embodiments, the data storage module 360 may store the processing result based on a private format. The private format may include a user-defined storage format, an encrypted format, or any combination thereof. It should be noted that the above description of the format is merely provided for the purposes of illustration, and not intended to limit the scope of the present disclosure. The user can read the processing result from the data storage module 360 by the human-computer interaction module 340 at any time and directly view the image without waiting for the execution of the processing operation, and thus, the image-viewing time of the user may be saved.

The data conversion module 370 may perform conversion processing on the processing result obtained by the data processing module 350 and/or may obtain a converted processing result. The conversion processing may include one or more of data format conversion, compression, encryption, or the like. The converted processing result may be stored in a first storage space 160 or other storage space by the data storage module 360. For example, the processing result may be converted into a digital imaging and communication in medicine (DICOM) format, and then stored in the first storage space 160. As another example, the processing result may be compressed, and then the compressed processing result may be stored in the first storage space 160. For safety reasons, the data conversion module 370 may perform one or more encryption operations on the processing result, and then the encrypted processing result may be stored in the first storage space 160. It should be noted that in a conversion operation, one or more conversion algorithms may be used.

It should be noted that the above description of the data processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the performance monitor 310 and the processing monitoring module 322 may be combined into one module.

Figure 4:
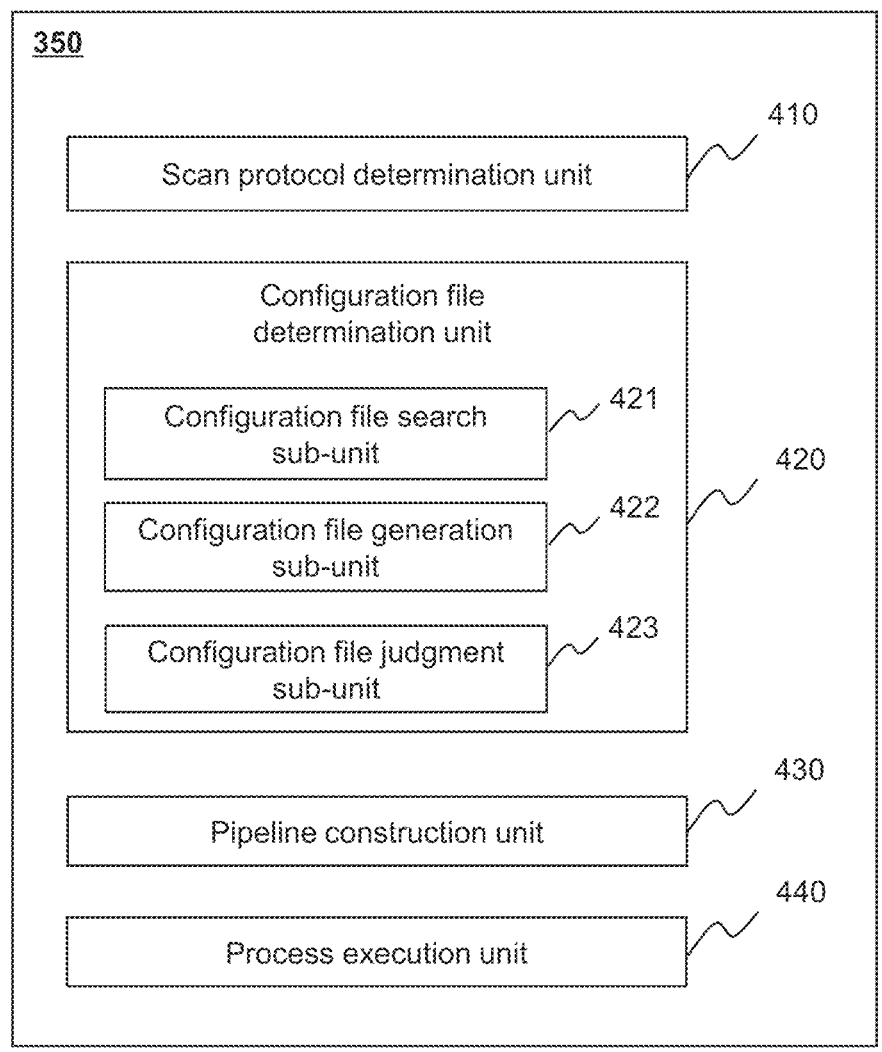
FIG. 4 is a schematic diagram illustrating an exemplary data processing module according to some embodiments of the present disclosure.

FIG. 4 is a schematic diagram illustrating an exemplary data processing module 350 according to some embodiments of the present disclosure. The data processing module 350 may include a scan protocol determination unit 410, a configuration file determination unit 420, a pipeline construction unit 430, and a process execution unit 440. The units may be directly and/or indirectly connected with each other. It should be noted that the data processing module 350 described in FIG. 4 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, two units thereof may be combined into one unit. As another example, one unit thereof may be segmented into two or more units.

The scan protocol determination unit 410 may determine a scan protocol of the image data. The scan protocol may include information relating to the scan object, the scan device (e.g., the imaging device), the scan parameters, or the like. The information relating to the scan object may include sexuality, weight, age, medical history, and biochemistry examination information of the patient, a scan position, a scan target site, or the like. The information relating to the scan device may include a device type, a device work state, device service lifespan, device service time, or the like. The information relating to the scan parameters may include imaging quality, scan speed, signal strength, a tomography direction and the corresponding number of image layers, an imaging modality, scan time, a voltage/current for the scan device, an irradiation dose, or the like, or any combination thereof. For example, CT scan parameters may include a tube voltage, a tube current, scan time, a layer thickness, a pitch, a scan volume, or the like. As another example, MRI scan parameters may include a diffused gradient magnetic field, diffusion sensitivity coefficients, pulse repetition interval time, echo time, or the like. In some embodiments, the scan protocol may include a data structure to store related parameters required for scanning and/or processing. The scan protocol may include device information relating to the scanning and/or processing. It should be noted that the form and specific content of the scan protocol may vary with different body sites, different devices, or different individuals.

In some embodiments, the scan protocol may be preset. The scan protocol may be automatically, semi-automatically, or artificially set. For example, the scan protocol determination unit 410 may automatically determine the scan parameters based on information relating to a scan object and/or a scan device. As another example, the user may perform modification on the automatically determined scan parameters. As a further example, the user may artificially set a scan protocol for a scanned target region. As a further example, the user may select a corresponding imaging device to scan the target region based on the scan parameters in the scan protocol to obtain the image data. The scan protocol may be preset based on information including, for example, sexuality, weight, age, medical history, biochemistry examination information of the patient, required image quality, scan region, image modality, or the like. In some embodiments, the above information may vary little in a scan protocol for similar patients, and thus, the scan protocol can be preset based on the information. In some embodiments, for one target region, there may be one or more preset scan protocols. The preset scan protocol(s) may be obtained by an experienced user through one or more experiments. In some embodiments, the scan protocol may be preset based on information relating to a clinic record of the patient. The information may include clinic indications, laboratory data, previous imaging reports, other reports from clinic examinations, or the like. The user (e.g., a radiologist) may preset a scan protocol applicable to the patient based on the information.

In some embodiments, the scan protocol determination unit 410 may parse a scan protocol based on incidental information of image data. In some embodiments, the image data stored in the DICOM standard may correspond to a DICOM image file. The scan protocol may be read from the DICOM image file and/or stored in the storage device (e.g., the hard disk 203, the read-only memory (ROM) 204, the random access memory (RAM) 206, the cloud memory, etc.). The DICOM image file can be used as a special format for medical image transmission and storage. The DICOM image file may contain image data, and/or the incidental information of the image data. The incidental information may include a scan protocol, for example, a patient unique identification, an imaging time, a target region, a key image position, a scan range (e.g., a chest CT scan, a brain CT scan, a MRI knee scan, etc.), a scan device, scan parameters, an examination information table, a sequence information table, an image information table, an image type, or the like, or a combination thereof. The patient unique identification may include, for example, a patient name, a patient number, or the like. In some embodiments, one target region of a patient may be examined for one or more times. One or more examinations may form an examination information table. One examination may have one or more examination sequences. One or more examination sequences may form one sequence information table. One examination sequence may correspond to one or more images. One or more images may form an image information table. Therefore, the information generated by one examination can form an examination information table, a sequence information table, an image information table, and a corresponding DICOM image file. In some embodiments, three information tables (e.g., an examination information table, a sequence information table, an image information table) may form an examination-sequence-image three-level data model. The relationship between the three information tables may be a hierarchical relationship. For example, the three types of information tables can be arranged in the order of the examination information table, the sequence information table, and the image information table from upper to lower. In some embodiments, the image information table may be associated with the DICOM image file. There may be a mapping relationship between the image information table and the DICOM image file. For example, the image information table may have a corresponding DICOM image file, and the DICOM image file may correspond to the image information table. According to the hierarchical relationship of the three information tables, the DICOM image file may correspond to an examination information table, and correspond to a sequence information table.

The configuration file determination unit 420 may determine a configuration file. The server 150 may perform data processing based on the configuration file. The server 150 may perform one or more processing functions based on the configuration file. In some embodiment, the configuration file may include names of one or more algorithms used in the data processing, a storage path of data, a storage path of the processing result, a processing flow (e.g., priority order for executing the algorithms), or the like. The server 150 may call and execute source codes of one or more corresponding algorithms based on related information and/or the flow in the configuration file to implement the data processing function(s). In some embodiments, the configuration file may include a script file for executing one or more programs. The script file may include a programming language related to an application program. The application program may include a browser (JavaScript, VBScript), a multimedia authoring tool, or the like. The script file may also include a macro of the application program and a batch processing language of an operating system. In some embodiments, the configuration file may include names and storage paths of one or more script files. In some embodiments, the configuration file may be a document in an extensible stylesheet language (XML) format or any other format.

In some embodiments, the server 150 may perform image data processing operation(s) on a DICOM image file based on a configuration file in the XML format. For example, the server 150 may perform one or more algorithms (e.g., registration, removing a bone, removing a bed board, etc.) on the cerebral perfusion image. As another example, the server 150 may perform a bone shielding operation on the acquired vessel CT image. As a further example, the server 150 may perform a processing operation (e.g., lung segmentation, trachea extraction, rib segmentation, vertebra segmentation, sternum segmentation, or the like, or a combination thereof) on a chest CT image.

In some embodiments, the configuration file determination unit 420 may determine a configuration file for a certain scan region and/or a certain image type. For example, for a brain MRI image, the configuration file determination unit 420 may determine a configuration file applicable to brain MRI image processing. As another example, for a chest CT image, the configuration file determination unit 420 may determine a configuration file applicable to chest CT image processing.

In some embodiments, the server 150 may modify the configuration file. In some embodiments, the user may set or modify the configuration file by the human-computer interaction module 340. For example, the server 150 or the user may modify the processing flow or the algorithm(s) in the configuration file, add or delete an algorithm name in the configuration file, or the like.

In some embodiments, the configuration file determination unit 420 may include a configuration file search sub-unit 421, a configuration file generation sub-unit 422, and a configuration file judgment sub-unit 423. The configuration file search sub-unit 421 may search a configuration file based on the image data acquired by the data acquisition module 330. In some embodiments, the configuration file search sub-unit 421 may search a configuration file in the XML format corresponding to a DICOM image file of the image data in the storage device based on a mapping relationship between the DICOM image file and the XML formatted file. In some embodiments, the configuration file search sub-unit 421 may perform search the configuration file by matching in the storage device based on the image type. The configuration file search sub-unit 421 may determine, based on the image type, whether there is a configuration file for processing an image of the image type. For example, for a brain MRI image, the configuration file search sub-unit 421 may search a configuration file corresponding to the brain MRI image.

The configuration file generation sub-unit 422 may generate a configuration file based on the image data acquired by the data acquisition module 330. In some embodiments, the configuration file generation sub-unit 422 may extract image information in the DICOM image file and determine, based on the image information, a processing algorithm required to be executed. In some embodiments, the configuration file generation sub-unit 422 may encode a corresponding algorithm name and/or a flow into an XML format file so as to generate a configuration file in the XML format corresponding to the DICOM image file. In some embodiments, the configuration file generation sub-unit 422 may generate corresponding configuration files based on different DICOM image files. Accordingly, the data processing device 120 may perform a corresponding program based on the configuration file to implement the image data processing function(s). For example, the data processing device 120 may perform one or more algorithms, such as registration, removing a bone and/or a bed board on the cerebral perfusion image. As another example, the data processing device 120 may perform processing, such as lung segmentation, trachea extraction, rib segmentation, vertebra segmentation, and/or sternum segmentation on the chest CT image.

The configuration file judgment sub-unit 423 may judge whether a second storage space stores data processing information corresponding to the image type based on the image data acquired by the data acquisition module 330. The second storage space may be located in a storage device inside or outside the server 150. The second storage space may be the same as or different from the first storage space 160. In some embodiments, the second storage space may refer to a storage space including a second storage location. In some embodiments, the server 150 may access the second storage space by searching the second storage location. For example, the server 150 may query and/or locate the second storage location, and then read some information from the second storage location. If the configuration file judgment sub-unit 423 determines that the second storage space does not store any data processing information corresponding to the image type to be processed, the server 150 may generate data processing information corresponding to the image type to be processed. If the configuration file judgment sub-unit 423 determines that the second storage space stores the data processing information corresponding to the image type to be processed, the server 150 may perform processing on the image using the data processing information stored in the second storage space, and/or obtain a processing result. The data processing information may include related information required for generating a configuration file. The data processing information may include one or more data processing algorithms and an execution order of the data processing algorithm(s).

The pipeline construction unit 430 may construct a data processing pipeline. In some embodiments, the pipeline construction unit 430 may construct a data processing pipeline based on the configuration file determined by the configuration file determination unit 420. In some embodiments, the pipeline construction unit 430 may construct one data processing pipeline based on a configuration file. The data processing pipeline may be executable codes of one or more operations. The executable codes may include source codes of one or more processing algorithms, one or more instructions for calling the source codes of the algorithm(s), one or more instructions for reading and/or writing data, and/or one or more related instructions to guide data to flow out of one algorithm module into another algorithm module. In some embodiments, the instructions may trigger the server 150 to create a corresponding data processing pipeline based on the instructions. In some embodiments, the data processing pipeline may exist in the form of a process, and when the server 150 receives the instructions, the server 150 may create a new data processing pipeline process. One data processing pipeline process may include one or more filters. The data processing pipeline filter(s) may have highly variability inside. For example, any two data processing pipeline filters in which an output data type and an input data type match with each other may be connected. The construction of the data processing pipeline may be extended in depth and/or width, which indicates that in the construction of the data processing pipeline, one filter may be connected to another filter or a plurality of other filters, and a plurality of filters may also be connected to one filter. When image processing is performed, a plurality of images can be processed in parallel to reduce the execution time of the data processing pipeline. Exemplary data processing pipelines may be illustrated in FIGS. 6-9.

The process execution unit 440 may execute a process based on the data processing pipeline constructed by the pipeline construction unit 430. During the execution of the process, the image data may be input into a data processing pipeline through a data source filter and transmitted through a pipe to one or more filters by which data processing operations may be performed, and then a processing result may be generated and output through a data root filter. In some embodiments, the server 150 may execute one or more data processing processes simultaneously. The data processing processes may perform different processing operations on the same image data or perform the same processing operation on different image data, or the like. In some implementations, the process execution unit 440 may execute the process after the process initiation module 321 initiates the process.

Figure 5:
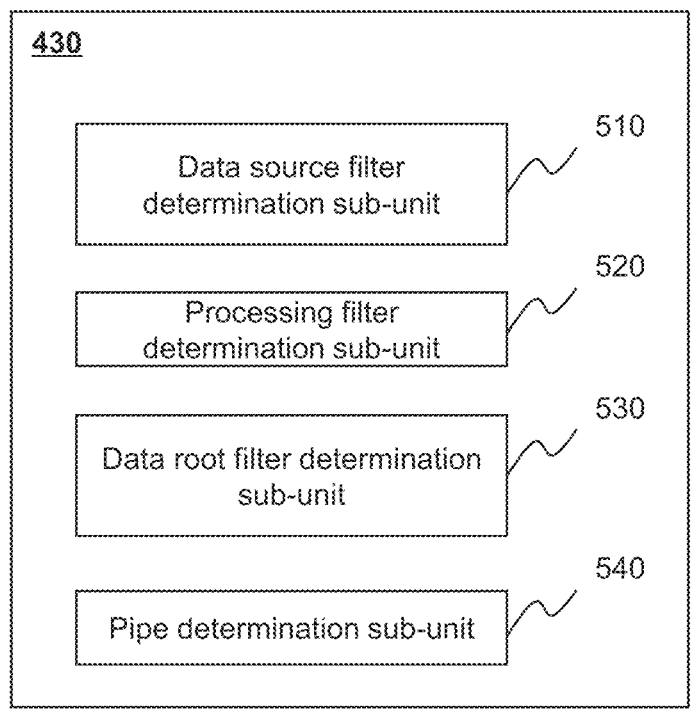
FIG. 5 is a schematic diagram illustrating an exemplary pipeline construction unit according to some embodiments of the present disclosure.

FIG. 5 is a schematic diagram illustrating an exemplary pipeline construction unit 430 according to some embodiments of the present disclosure. The pipeline construction unit 430 may include a data source filter determination sub-unit 510, a processing filter determination sub-unit 520, a data root filter determination sub-unit 530, and a pipe determination sub-unit 540.

The data source filter determination sub-unit 510 may determine one or more data input ports based on a configuration file. A data source filter may introduce the image data acquired by the data acquisition module 330 into the processing pipeline. In some embodiments, the data source filter may be configured with one or more data read instructions. The data input port(s) may include data input way(s), data type(s), data name(s), paths of input data, or the like. In some embodiments, the data source filter determination sub-unit 510 may modify the data input ports. For example, the data source filter determination sub-unit 510 may automatically modify the data input ports based on a modified configuration file. The modification may include adding a new data input port, deleting an existing data input port, changing information of an existing data input port, or the like.

The processing filter determination sub-unit 520 may determine one or more processing filters based on a configuration file. A filter may be configured with one or more algorithm modules (e.g., image denoising, image enhancement, image splicing, image segmentation, etc.) required for implementing a processing function of the configuration file. The filter(s) may include an image processing filter. The image processing filter may determine a minimum density of the image, a maximum density of the image, an average density of the image, or the like. The image processing filter may determine a minimum diameter, a maximum diameter, a volume, an elongation, a surface area and/or a sphericity of a certain tissue or organ in the image, or the like. One filter may implement one or more processing functions, or a portion of one processing function. In some embodiments, the processing filter determination sub-unit 520 may determine one or more processing filters based on an algorithm name of a configuration file. For example, the processing filter determination sub-unit 520 may extract source codes of an algorithm based on an algorithm name of the configuration file, or generate an instruction for calling the source codes of the algorithm, or the like.

In some embodiments, the data processing device 120 may have one or more filter databases. The filter database(s) may include one or more algorithms which may be used in processing and/or corresponding algorithm source codes. The filter databases may be stored in the memory device or any other external data source. The filter database(s) may include one or more filters set in the configuration file. In some embodiments, the server 150 may reconfigure one or more filters. For example, the server 150 may add a new filter, or update an existing filter in a filter database. As another example, the server 150 may reconfigure a filter in a configuration file through, e.g., adding, changing, or deleting a filter name in the configuration file. In some embodiments, the user may send a corresponding instruction to the server 150 by the user interface 201 to reconfigure a filter. In some embodiments, the user may edit a file related to a filter by the user interface 201, so as to implement reconfigure the filter.

The data root filter determination sub-unit 530 may determine one or more data root filters based on a configuration file. The data root filters may output the processed image data from the data processing pipeline. In some embodiments, the data root filters may be configured with one or more data output and/or write instructions. The data output ports may include data output way(s), data type(s), data name(s), paths of output data, or the like. In some embodiments, the data root filter determination sub-unit 530 may modify the data output ports. For example, the data root filter determination sub-unit 530 may automatically modify the data output ports based on a modified configuration file. The modification may include adding a new data output port, deleting an existing data output port, changing information of the existing data output port, or the like.

The pipe determination sub-unit 540 may determine a connection pipe between a data source filter, a processing filter, and/or a data root filter based on a configuration file. The pipe may include one or more instructions to guide data flowing out of a data source filter or a processing filter. The pipe may include one or more instructions to guide data flowing into the filter or the data root filter. In some embodiments, the pipe may also provide temporary storage for data required to be used by the data root filter or the filter (e.g., the data is stored on the hard disk 203, the ROM 204, the RAM 206, the memory 216, the storage 219, etc.).

In some embodiments, the pipeline construction unit 430 may construct a data processing pipeline based on a data source filter, a data root filter, a processing filter, and/or a pipe in a configuration file. In some embodiments, at least one data source filter as well as at least one data root filter may be directly or indirectly connected through a pipe to form a data processing pipeline. In some embodiments, at least one data source filter, at least one filter, and/or at least one data root filter may be directly or indirectly connected through one or more pipes to form a data processing pipeline. The image data may enter a data processing pipeline through a data source filter, and may be transmitted through one or more pipes to one or more filters. The one or more filters may perform data processing, and finally a data root filter may output the processing result(s). In some embodiments, a plurality of filters may process the same data, the pipeline construction unit 430 may connect the filters in parallel to improve the execution efficiency of the data processing pipeline. In some embodiments, a data source filter may transmit the image data to filter. The filter may perform processing on the image data based on one or more data processing algorithms and output an intermediate processing result to another filter. The other filter may continue performing data processing on the intermediate processing result based on one or more data processing algorithms and output a final processing result to a data root filter, and thus, the processing of the image data is completed.

Figure 6:
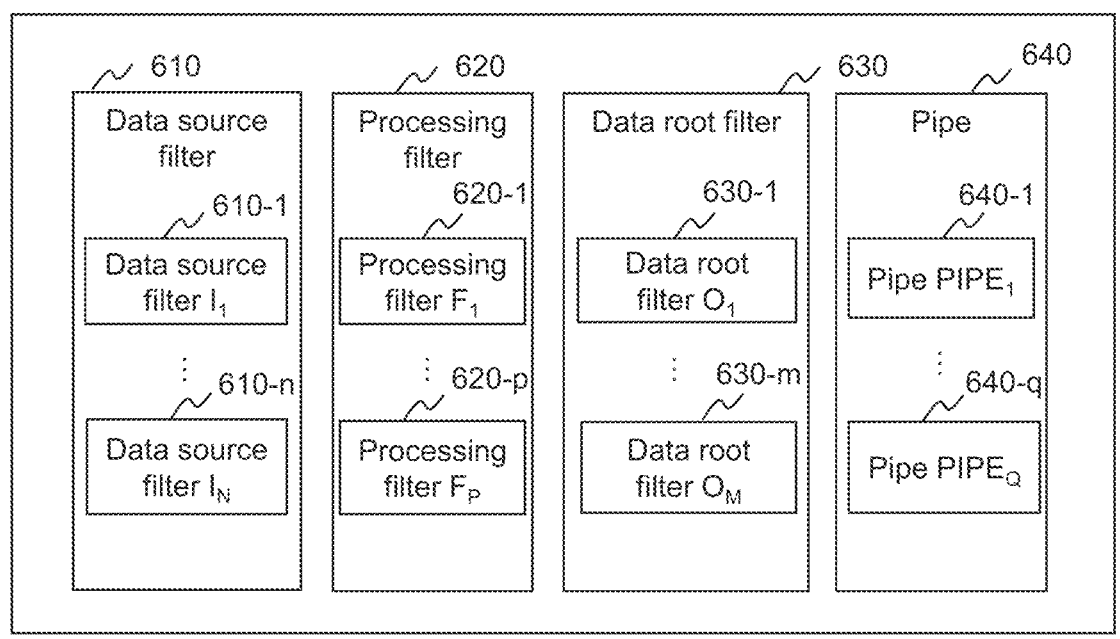
FIG. 6 is a schematic diagram illustrating an exemplary data processing pipeline according to some embodiments of the present disclosure.

FIG. 6 is a schematic diagram illustrating an exemplary data processing pipeline according to some embodiments of the present disclosure. The data processing pipeline may include one or more data source filters 610 (e.g., a data source filter $I_1$ 610-1, a data source filter $I_2$ 610-2 (not shown), . . . , a data source filter $I_N$ 610-n, etc.), one or more processing filters 620 (e.g., a processing filter $F_1$ 620-1, a processing filter $F_2$ 620-2, . . . , a processing filter $F_P$ 620-p, etc.), one or more data root filters 630 (e.g., a data root filter $O_1$ 630-1, a data root filter $O_2$ 630-2, . . . , a data root filter $O_M$ 630-m, etc.), and one or more pipes (e.g., a pipe $PIPE_1$ 640-1, a pipe $PIPE_2$ 640-2, a pipe $PIPE_Q$ 640-q, etc.). The numbers N, M, P, and Q are all integers greater than 0. In some embodiments, the numbers N, M, P, and Q may be all the same. In some embodiments, part of the numbers may be the same. In some embodiments, the numbers may be different. For example, one data processing pipeline may include one data source filter 610, two data root filters 630, three processing filters 620, and five pipes 640. As another example, one data processing pipeline may include two data source filters 610, one data root filters 630, three processing filters 620, and six pipes 640. The number n may be an integer in the range [1, N]. The number m may be an integer in the range [1, M]. The number p may be an integer in the range [1, P]. The number q may be an integer in the range [1, Q].

The processing filter 620 may include a processing algorithm for the image data. The processing algorithm may be removing of a bed board, vessel segmentation, organ segmentation, colon segmentation, image splicing, lung nodule segmentation, cerebral perfusion, body perfusion, or the like, or a combination thereof. The processing filter 620 may be an image processing filter. The image processing filter may include a brightness and/or contrast operation filter, a color change filter, a smoothing filter, a sharpness adjustment filter, a rotary filter, a stretch filter, a compression filter, or the like. In some embodiments, in one data processing pipeline, the server 150 may call the same filter for one or more times.

In some embodiments, the pipe 640 may receive data of the data source filter 610, and/or may provide temporary storage of the data for a short time, so that a next processing filter 620 may read required data from the pipe. In some embodiments, the pipe 640 may receive data of the processing filter 620, and may provide temporary storage of the data for a short time, so that a next data root filter 630 may read required data from the pipe. The pipe 640 may include executable code(s), and/or any parameter required for executing the code(s). In some embodiments, the pipe may not process the received data. In some embodiments, the pipe may perform format conversion on the data output from a previous filter as required, to match the data input format of a next filter.

In some embodiments, the data source filter 610 may be regarded as a first specific filter. The processing performed by the first special filter on data may include data input. In some embodiments, the data root filter 630 may be regarded as a second specific filter. The processing performed by the second special filter on data may include data output. In some embodiments, the pipe 640 may connect one or more data source filters 610, one or more processing filters 620, and/or one or more data root filters 630, so as to form a data processing pipeline.

Figure 7A:
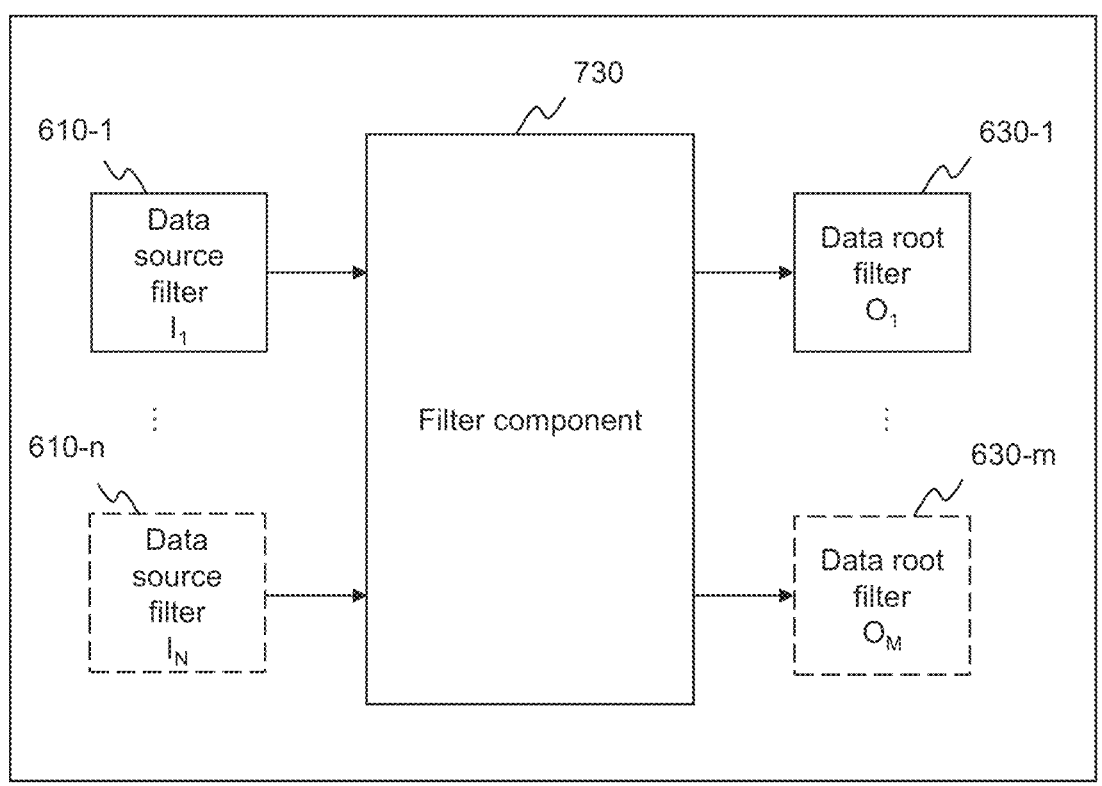
FIG. 7A is a schematic diagram illustrating a structure of an exemplary data processing pipeline according to some embodiments of the present disclosure.

FIG. 7A is a schematic diagram illustrating a structure of an exemplary data processing pipeline 700 according to some embodiments of the present disclosure. The data processing pipeline 700 may be constructed from the pipeline construction unit 430. The data processing module 350 may execute a corresponding process based on the data processing pipeline 700. The data processing pipeline 700 may include one or more data source filters such as the data source filter $I_1$ 610-1, ..., the data source filter $I_N$ 610-n, one or more data root filters such as the data root filter $O_1$ 630-1, ..., the data root filter $O_M$ 630-m, a filter component 730. The filter component 730 may include one or more processing filters, and pipes for connecting the data source filters, the data root filters, and the processing filters (not shown in figures).

In some embodiments, the image data acquired by the data acquisition module 330 may be input into the data processing pipeline 700 via a data source filter $I_1$ 610-1, ..., and/or a data source filter $I_N$ 610-n. There may be various connection ways between the data source filter(s) and the data root filter(s) in the data processing pipeline 700. The correspondence of the number of data source filter(s) and the number of data root filter(s) may be one-to-one, one-to-many, many-to-one, many-to-many, or the like. For example, the data processing pipeline 700 may generate one or more sets of processed data based on the data input via the data source filter $I_1$ 610-1 through the filter component 730. As another example, the data processing pipeline 700 may input a plurality of sets of data from the data source filter $I_1$ 610-1, ..., and/or the data source filter $I_N$ 610-n to the filter component 730, and generate one or more sets of processed data through the filter component 730. In some embodiments, the data processing pipeline 700 may output the one or more sets of processed data to the data root filter $O_1$ 630-1, ..., and/or the data root filter $O_M$ 630-m. In some embodiments, the data processing pipeline 700 may output different sets of processed data to different data root filters.

In some embodiments, the data processed by the filter component 730 may be output through the data root filter $O_1$ 630-1, ..., and/or the data root filter $O_M$ 630-m. The data output through the data root filters may be further transmitted to the input/output component 205 for display, and/or may be further stored in the memory device or an external data source. The processing result may be stored in a DICOM format, in a compressed format, and/or in an encrypted format.

In some embodiments, the filter component 730 may include one or more processing filters connected by one or more pipes. The processing filters in the filter component 730 may be in a series connection, a parallel connection, and/or a series-parallel connection. The filter component 730 may include one or more processing filters and/or one or more pipes for connecting the filters. The one or more processing filters in the filter component 730 may execute a same processing algorithm, or may execute different processing algorithms. The connection ways of the filters may include a series connection (FIG. 7B), a parallel connection (FIG. 7C), and/or a series-parallel connection (FIG. 7D).

Figure 7B:
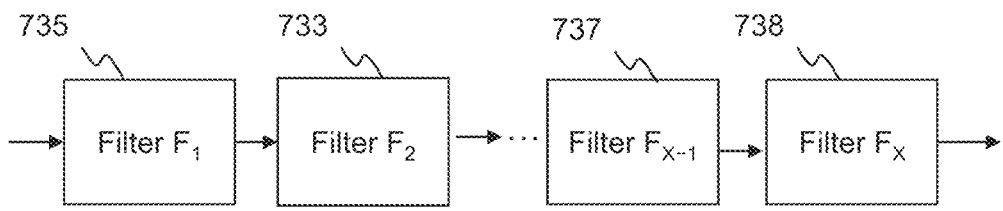
FIG. 7B is a schematic diagram illustrating a series structure of an exemplary filter component according to some embodiments of the present disclosure.

FIG. 7B is a schematic diagram illustrating a series structure of an exemplary filter component 730 according to some embodiments of the present disclosure. Two or more processing filters (e.g., the filter $F_1$ 735, ..., and the filter $F_X$ 738, etc.) may be connected in series. If the processing filters are in series connection, the output data of the filter $F_1$ 735 may be only input to the filter $F_2$ 733, the output data of the filter $F_{X-1}$ 737 may be only input to the filter $F_X$ 738, and then the output data of the filter $F_X$ 738 may enter a data root filter. The number X may be an integer greater than 0.

Figure 7C:
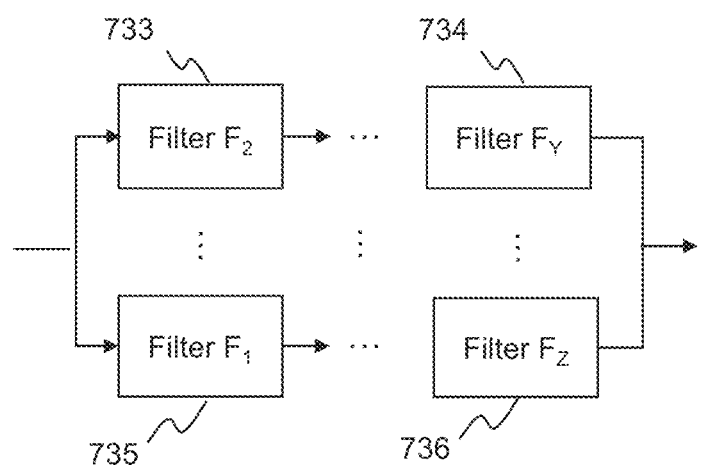
FIG. 7C is a schematic diagram illustrating a parallel structure of an exemplary filter component according to some embodiments of the present disclosure.

FIG. 7C is a schematic diagram illustrating a parallel structure of an exemplary filter component 730 according to some embodiments of the present disclosure. As shown in FIG. 7C, processing filters $F_2$ 733, ..., and $F_Y$ 734 may be in a series connection and may be connected in parallel with filters $F_1$ 735, ..., and $F_Z$ 736 that may be in series connection. If the processing filters are connected in parallel, data from a previous filter or a data source filter may be input into parallel filters $F_2$ 733, ..., and $F_1$ 735 simultaneously, and the output data of each filter in parallel may only flow through a filter or a data root filter in series connection therewith. It should be noted that in some embodiments, the filter $F_2$ 733 may not be connected in series with the filter $F_Y$ 734, but may be directly connected in parallel with the filter $F_1$ 735. In some embodiments, the filter $F_1$ 735 may not be connected in series with the filter $F_Z$ 736, but may be directly connected in parallel with the filter $F_2$ 733.

Figure 7D:
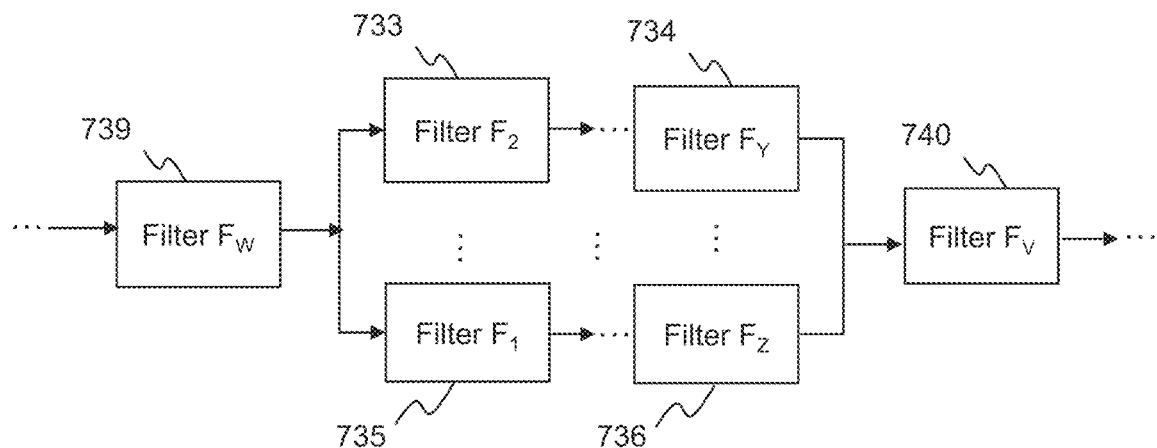
FIG. 7D is a schematic diagram illustrating a series-parallel structure of an exemplary filter component according to some embodiments of the present disclosure.

FIG. 7D is a schematic diagram illustrating a series-parallel structure of an exemplary filter component 730 according to some embodiments of the present disclosure. In some embodiments, processing filters in parallel connection may be connected in series with one or more filters (e.g., the filter $F_W$ 739, . . . , the filter $F_V$ 740, etc.), so that filters may be connected in series-parallel.

It should be noted that the processing filter(s) in series connection shown in FIG. 7B, the processing filter(s) in parallel connection shown in FIG. 7C, and the processing filter(s) in series-parallel connection shown in FIG. 7D are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing filters in the filter component 730 may be arbitrarily combined, arranged, and/or connected based on the basic series connection and parallel connection, and the filter component 730 may either extend in depth (i.e., by increasing the serial length of the data processing pipeline) or extend in width (i.e., by increasing the number of filters in parallel connection in the data processing pipeline).

Figure 8:
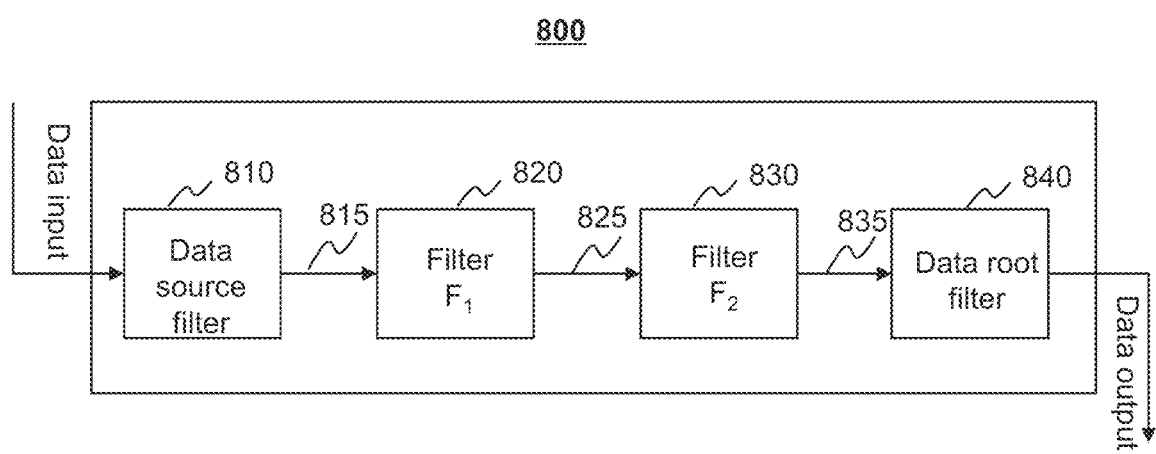
FIG. 8 is a schematic diagram illustrating an exemplary data processing pipeline according to some embodiments of the present disclosure.

FIG. 8 is a schematic diagram illustrating an exemplary data processing pipeline 800 according to some embodiments of the present disclosure. The data processing pipeline 800 may include a data source filter 810, a processing filter $F_1$ 820, a processing filter $F_2$ 830, and a data root filter 840. The filter $F_1$ 820 and the filter $F_2$ 830 may be connected in series. The image data (e.g., brain CT image data) may be input to the data processing pipeline 800 through the data source filter 810 and then be input to the filter F 820 through a pipe 815. A first processing (e.g., removing a bed board in the brain CT image) may be performed on the image data in the filter $F_1$ 820 and then the image data may be input to the filter $F_2$ 830 through a pipe 825. A second processing (e.g., removing a bone in the brain CT image) may be performed on the image data in the filter $F_2$ 830 and then the image data may be input to the data root filter 840 through a pipe 835. In some embodiments, data input to the data root filter 840 may be further transmitted to the input/output component 205 for display, or may be transmitted to a storage device or another external data source for storage.

Figure 9:
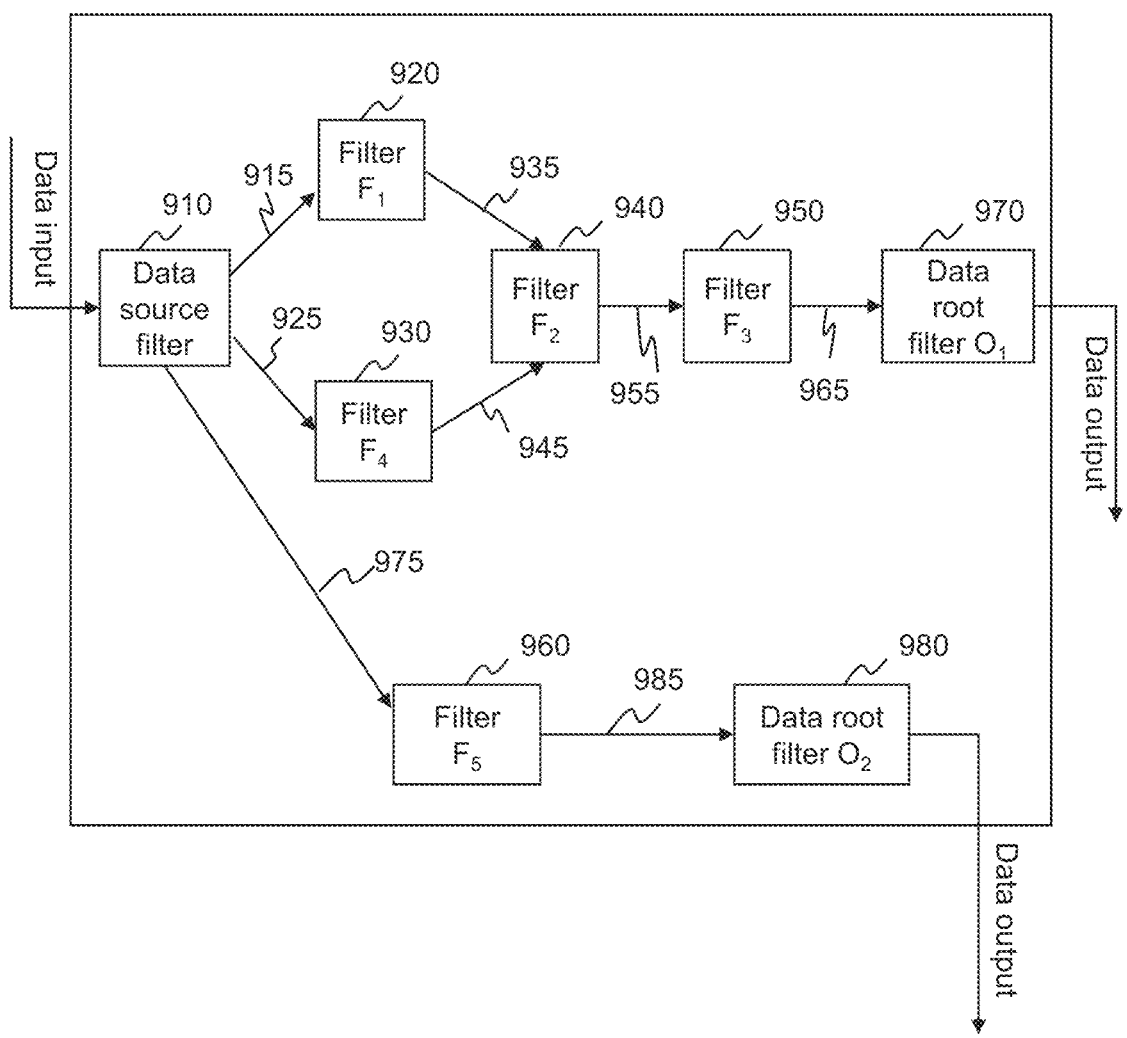
FIG. 9 is a schematic diagram illustrating an exemplary data processing pipeline according to some embodiments of the present disclosure.

FIG. 9 is a schematic diagram illustrating an exemplary data processing pipeline 900 according to some embodiments of the present disclosure. The data processing pipeline 900 may include a data source filter 910, a processing filter $F_1$ 920, a processing filter $F_4$ 930, a processing filter $F_2$ 940, a processing filter $F_3$ 950, a processing filter $F_5$ 960, a data root filter $O_1$ 970, and a data root filter $O_2$ 980. The filter $F_1$ 920, the filter $F_4$ 930, the filter $F_2$ 940, the filter $F_3$ 950, and the filter $F_5$ 960 may be connected in series-parallel. For example, the filter $F_1$ 920 and the filter $F_4$ 930 may be connected in parallel. The $F_1$ 920 and the filter $F_4$ 930 may be connected in series with the filter $F_2$ 940 and the filter $F_3$ 950.

On the one hand, the image data may be input to the data processing pipeline 900 through the data source filter 910 and then be input to the filter $F_1$ 920 through a pipe 915 and the filter $F_4$ 930 through a pipe 925. The image data may be input to the filter $F_2$ 940 through the pipe 935 after being processed in the filter $F_1$ 920. The image data may enter the filter $F_2$ 940 through the pipe 945 after being processed in the filter $F_4$ 930. The image data may be input to the filter $F_3$ 950 through the pipe 955 after being processed in the filter $F_2$ 940. The image data may be input to the data root filter $O_1$ 970 through the pipe 965 and may be output after being processed in the filter $F_3$ 950. On the other hand, the image data may be input to the data processing pipeline 900 through the data source filter 910 and then be input to the filter $F_5$ 960 through the pipe 975. The image data may be input to the data root filter $O_2$ 980 through the pipe 985 and be output after being processed in the filter $F_5$ 960. In some embodiments, data input to the data root filter $O_1$ 970 and/or the data root filter $O_2$ 980 may be further transmitted to the input/output component 205 for display, or may be transmitted to a storage device or another external data source for storage.

In some embodiments, two or more of the filter $F_1$ 920, the filter $F_4$ 930, the filter $F_2$ 940, the filter $F_3$ 950, and the filter $F_5$ 960 may be the same. For example, the filter $F_1$ 920 and the filter $F_5$ 960 may be the same, indicating that a same processing may be performed on the same or different image data.

Figure 10A:
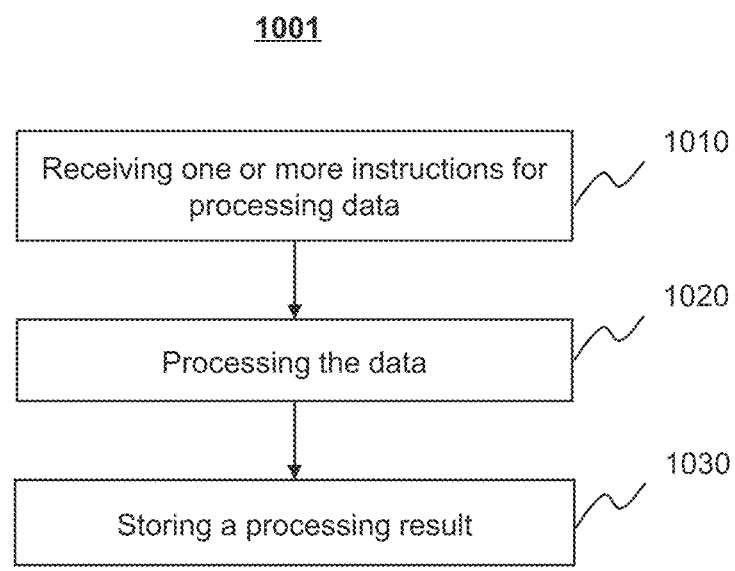
FIG. 10A is a flowchart illustrating an exemplary process for processing image data according to some embodiments of the present disclosure.

FIG. 10A is an exemplary flowchart illustrating an exemplary process 1001 for processing image data according to some embodiments of the present disclosure. The process 1001 may include receiving one or more instructions for processing data 1010, processing the data 1020, and storing a data processing result 1030.

In 1010, one or more processing instructions may be received. In some embodiments, operation 1010 may be performed by the human-computer interaction module 340. In some embodiments, the processing instruction(s) may include one or more processing algorithm required to be performed on the image data acquired by the data acquisition module 330 to facilitate image-viewing for the user. The processing instruction(s) may include adjusting the window width and/or window level of the received medical image, scaling the medical image, measuring and/or annotating the received medical image, managing patients' data, performing two-dimensional and/or three-dimensional image processing on the medical image, reconstructing the medical image using a three-dimensional volume technique, performing three-dimensional view adjustment and color adjustment on the medical image, and performing automatic editing and volume measurement on a target region of the medical image. In some embodiments, the processing instruction(s) may include a processing instruction for a medical image, a thumbnail, or a detection number, or the like. The thumbnail may be a compressed medical image with a reduced resolution. The detection number may correspond to a medical image scanning at a certain time or of a batch.

In some embodiments, the processing instruction(s) may be input by a user via the user interface 201. For example, the user may input the processing instruction(s) on a software interface of the data processing device 120. As another example, the user may input the processing instruction(s) on a command line in the operation system of the server 150. In some embodiments, the processing instruction(s) may be sent to the server 150 via the terminal 140 by the user. In some embodiments, the server 150 may analyze the received processing instruction(s) and/or determine the image data and/or algorithm required for subsequent processing. For example, if the server 150 receives a detection number, the server 150 may search corresponding image data based on the detection number, and then determine the processing algorithm required to be executed based on the content or image type of the image data. As another example, if the server 150 receives a thumbnail, the server 150 may determine the processing algorithm required to be executed and/or corresponding image data (e.g., original data of a chest CT image corresponding to the thumbnail of the chest CT image) according to contents shown in the thumbnail (e.g., the thumbnail of the chest CT image).

In 1020, the data may be processed. Operation 1020 may be performed by the processing module 350. In some embodiments, the data processing module 350 may process the data based on one or more data processing processes. In some embodiments, the data processing process(es) may include one or more algorithms required by the data processing pipeline constructed by the server 150 based on the configuration file. In some embodiments, the data acquisition module 330 may acquire the image data according to the processing instruction(s) received in 1010. In some embodiments, the data processing module 350 may execute the processing process(es) based on the processing instruction(s). For example, the data processing module 350 may execute one or more processing operations, such as registering, removing a bone and/or a bed board, or the like, on an acquired cerebral perfusion image. As another example, the data processing module 350 may execute a masking operation of a bone on an acquired vessel CT image. In some embodiments, the data processing module 350 may execute one or more possible processing operations relating to the image data. For example, if the acquired image data is a chest CT image, the data processing module 350 may perform all processing operations associated with the chest CT image and may be required for facilitating the image-viewing of the user including, for example, lung segmentation, trachea extraction, rib segmentation, vertebra segmentation, sternum segmentation, etc.

In 1030, the processing result generated in 1020 may be stored. The result may include an intermediate result and/or a final result generated in the processing operation 1020. Operation 1030 may be performed by the data storage module 360. The data storage module 360 may store the processing result in the storage device (e.g., a hard disk 203, a read only memory (ROM) 204, a random access memory (RAM) 206, etc.) or send the processing result to the terminal 140 via the network 130 for storage. In some embodiments, the data storage module 360 may transmit the processing result to an external data source (e.g., a cloud memory, etc.) via the network 130 for storage. In some embodiments, the data storage module 360 may store the processing result based on a private format. In some embodiments, the data storage module 360 may store the processing result after the processing result is encrypted. In some embodiments, the server 150 may display the processing result, for example, in the user interface 201 or the display module 212.

Figure 10B:
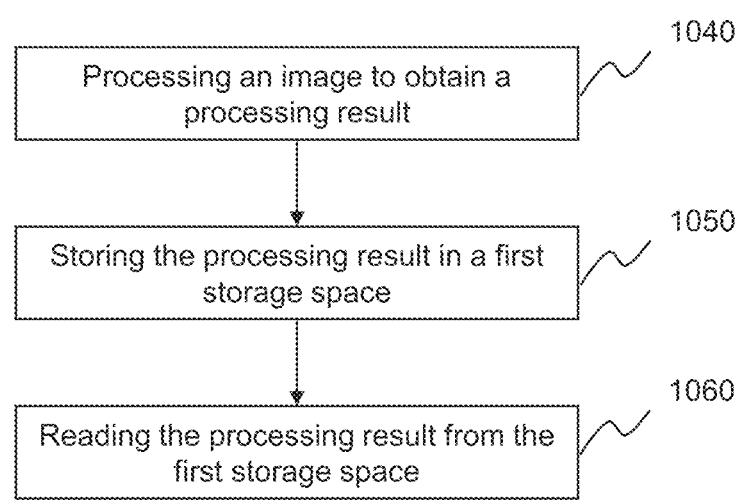
FIG. 10B is a flowchart illustrating an exemplary process for processing image data according to some embodiments of the present disclosure.

FIG. 10B is an exemplary flowchart illustrating an exemplary process 1002 for processing image data according to some embodiments of the present disclosure. The process 1002 may include processing an image 1040, storing a processing result 1050, and reading the processing result 1060.

In 1040, an image may be processed to obtain a processing result. In some embodiments, the same processing may be performed in operation 1040 as operation 1020. Operation 1040 may be performed by the data processing module 350. In some embodiments, in 1040, an image type may be acquired, and at least one data processing algorithm required in processing the image may be determined according to the image type. The image may be processed using the at least one data processing algorithm to obtain the processing result.

In 1050, the processing result may be stored in a first storage space 160. Operation 1050 may be performed by the data storage module 360. In some embodiments, before the processing result is stored in the first storage space 160, the data conversion module 370 may perform a conversion operation on the processing result to obtain a conversed processing result. The conversion operation may include at least one of format conversion, compression, encryption, or the like. For example, format conversion may be performed on the processing result, the processing result may be converted to a DICOM format, and then the converted processing result may be stored in the first storage space 160. The compression operations may be performed on the processing result obtained by the server 150, and then the compressed processing result may be stored in the first storage space 160. In some embodiments, for safety reasons, encryption operation may be performed on the processing result obtained by the server 150, and then the encrypted processing result may be stored in the first storage space 160. In some embodiments, one or more conversion operations may be performed on the processing result.

In 1060, one or more terminals 170 may read the processing result from the first storage space 160. In some embodiments, the one or more terminals 170 may read the processing result from the first storage space 160 directly. In some embodiments, the one or more terminals 170 may perform inverse conversion (e.g., format conversion, decompression, decryption, etc.) on the read processing result, so that the user may view the image processing result normally.

Figure 11:
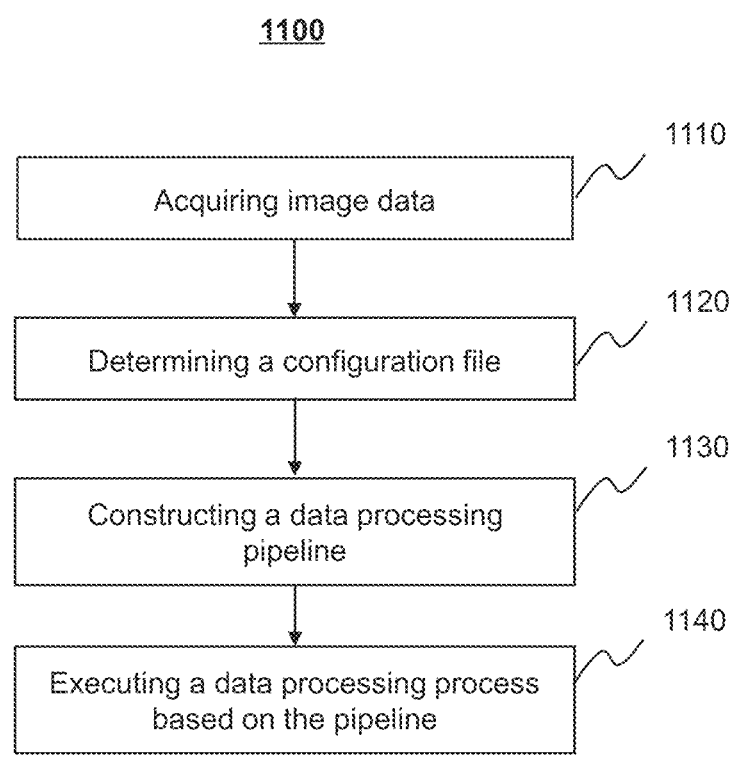
FIG. 11 is a flowchart illustrating an exemplary process for processing image data according to some embodiments of the present disclosure.

FIG. 11 is a flowchart illustrating an exemplary process 1110 for processing image data according to some embodiments of the present disclosure. In some embodiments, the process 1110 may be performed by the data processing module 350. The process 1110 may include acquiring image data 1110, determining a configuration file 1120, constructing a data processing pipeline 1130, and executing a data processing process 1140.

In 1110, image data may be acquired. Operation 1110 may be performed by the data acquisition module 330. In some embodiments, the data acquisition module 330 may acquire the image data based on the processing instruction received in 1010. In some embodiments, the acquired image data may include image information of one or more target regions, such as a lung image, an abdominal image, a brain image, a heart image, a vertebra image, or the like, or any combination thereof. The acquired image data may be original image data or processed image data. In some embodiments, the acquired image data may include an MRI image, a CT image, a PET image, a CT-PET image, a SPECT image, or the like, or any combination thereof. In some embodiments, the image data may be acquired from the imaging device 110 directly or from the terminal 140 (e.g., via the network 130), or read from a storage device (e.g., the hard disk 203, the read-only memory (ROM) 204, the random access memory (RAM) 206, etc.), the input/output component 205, a cloud memory, or the like.

In 1120, the configuration file may be determined. Operation 1120 may be performed by the configuration file determination unit 420. In some embodiments, the server 150 may determine the configuration file based on the processing instruction received in 1010 and/or the image data acquired in 1120. In some embodiments, the server 150 may determine whether a matched configuration file exists based on the processing instruction received in 1010 and/or the image data acquired in 1120. In some embodiments, the server 150 may generate the configuration file based on the processing instruction received in 1010 and/or the image data acquired in 1120.

In 1130, a data processing pipeline may be constructed. Operation 1130 may be performed by the pipeline construction unit 430. In 1130, the pipeline construction unit 430 may construct the data processing pipeline based on the configuration file determined in 1120. Specifically, the server 150 may read the configuration file, assemble a data source filter, a data root filter, a processing filter and one or more pipes based on the configuration file so as to complete the construction of the data processing pipeline. The image data may be input to the data processing pipeline through the data source filter, may be transmitted to one or more processing filters through the pipeline, may be processed by the one or more processing filters, and finally the processing result may be output by the data root filter.

In 1140, a data processing process may be executed. Operation 1140 may be performed by the process execution unit 440. In some embodiments, the process execution unit 440 may execute the process based on the data processing pipeline constructed in 1130. If the processing process is executed, the image data may be input to the data processing pipeline through the data source filter, may be transmitted to one or more processing filters through the pipe(s) and processed by the one or more processing filters, and finally the processing result may be output by the data root filter. In some embodiments, the server 150 may execute one or more data processing processes simultaneously. The one or more data processing processes may perform different operations on the same image data, or perform the same operations on different image data, or the like.

Figure 12:
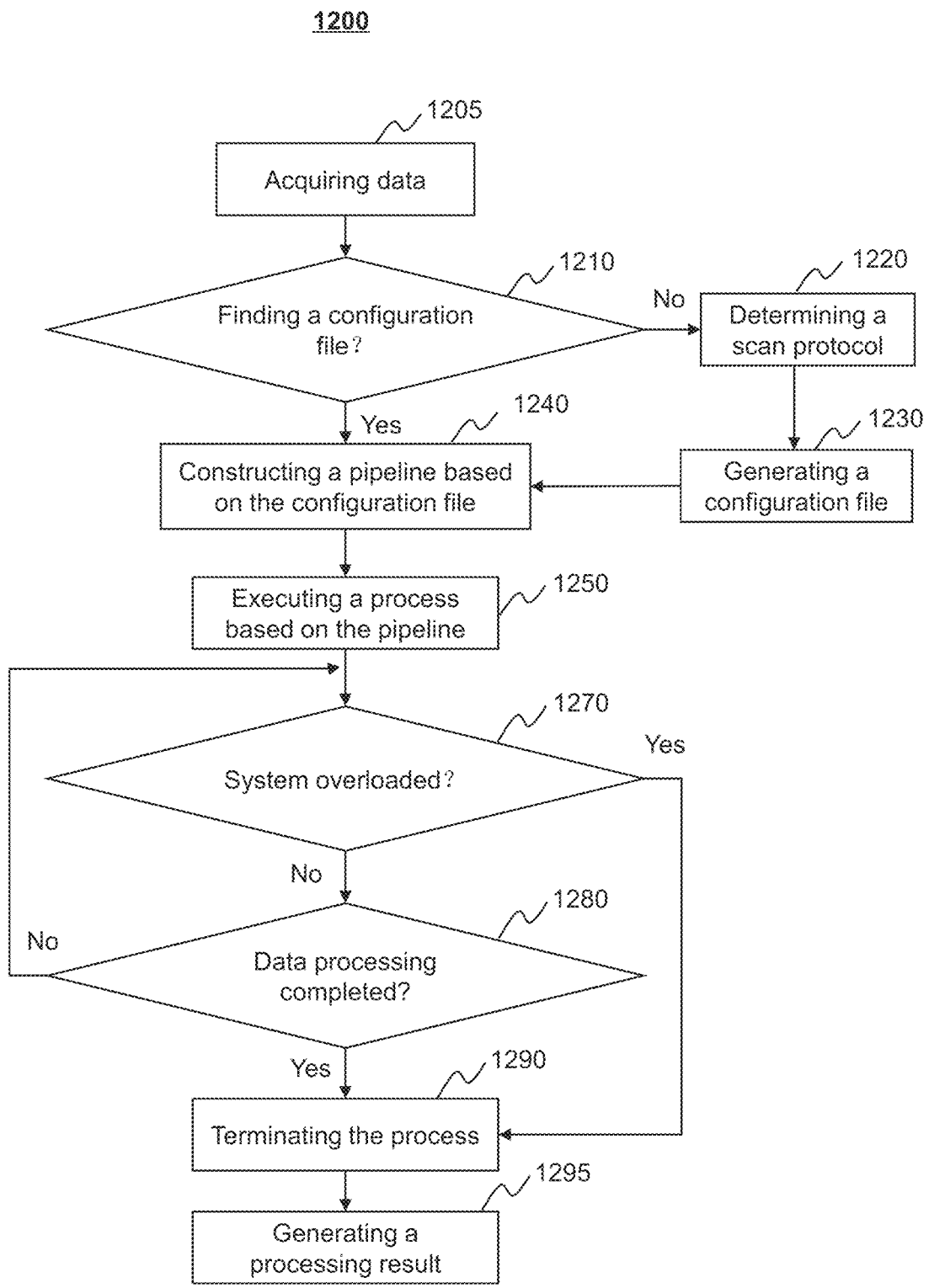
FIG. 12 is a flowchart illustrating an exemplary process for processing image data according to some embodiments of the present disclosure.

FIG. 12 is a flowchart illustrating an exemplary process 1200 for processing image data according to some embodiments of the present disclosure. In some embodiments, the process 1200 may be performed by the data processing module 350.

In 1205, data may be acquired. The data may be image data. In some embodiments, operation 1205 may be performed by the data acquisition module 330. In some embodiments, the image data may include image information of one or more target regions, such as a lung image, an abdominal image, a brain image, a heart image, a vertebra image, or the like, or any combination thereof. The image data may be original image data or processed image data, or the like. In some embodiments, the image data may include an MRI image, a CT image, a PET image, a CT-PET image, a SPECT-MRI image, or the like, or any combination thereof. In some embodiments, the image data may be acquired from the imaging device 110 directly or from the terminal 140 via the network 130, or read from a storage device (e.g., the hard disk 203, the read-only memory (ROM) 204, the random access memory (RAM) 206, etc.), the input/output component 205, a cloud memory, or the like.

In 1210, a configuration file may be searched. Operation 1210 may be performed by the configuration file search sub-unit 421. In some embodiments, if a scanning of the target region is completed, the server 150 may generate a sequence information table, an image information table, and/or a DICOM image file associated with the image data of the target region. The image information table of the image data may be associated with the DICOM image file. For example, there may be a mapping relationship between the image information table and the DICOM image file, indicating that the image information table may correspond to a DICOM file, or the DICOM file may correspond to an image information table. In some embodiments, the server 150 may search the configuration file of the XML format corresponding to the DICOM image file of the image data in the storage device based on the mapping relationship between the DICOM image file and the XML document.

In some embodiments, the server may perform a matching search in the storage device (e.g., the hard disk 203, the read-only memory (ROM) 204, the random access memory (RAM), or other storage devices) based on the type of the image data acquired in 1205. The matching search may refer to searching whether there is a configuration file for processing image data according to the image type of the image data. For example, for a brain MRI image, the configuration file search sub-unit 421 may search a configuration file for processing the brain MRI image.

In some embodiments, the image data may include additional information, such as a scan condition, a scan range, a key image location, a check unique identification (check UID), a sequence unique identification (sequence UID), an image type, an image unique identification UID (image UID), an image data storage path, a DICOM image file, or the like, or any combination thereof. The server 150 may search the configuration file matching the image type based on the additional information of the image data.

In some embodiments, the server 150 may perform one or more functional processing operations on the image data based on the configuration file. For example, if the image data acquired in 1205 is a lung image, the server 150 may search whether there are one or more configuration files for processing the lung image based on the lung image data. The server 150 may process the lung image based on the configuration file. The processing of the lung image based on the configuration file may include one or more of lung segmentation, lung vessel segmentation, lung trachea segmentation, or the like.

In some embodiments, the configuration file may be stored in the storage device (e.g., the hard disk 203, the read-only memory (ROM) 204, the random access memory (RAM) 206, or other storage devices) in the form of a DICOM tag. The DICOM tag may include one or more pieces of information, such as a checking unit, a checking physician ID, a capturing position, a capturing angle, a capturing distance, an image exposure mode, an exposure parameter, environmental information, device information, a device maintenance status, device configuration information, an image generation time, user information, a patient's medical record, a diagnostic report, prescription information, or the like, or any combination thereof. In some embodiments, the server 150 may compare the image data with the information in the DICOM tag. If the image data is the same as or similar to one or more pieces of information in the DICOM tag, it may indicate that the configuration file corresponding to the image data is found.

In some embodiments, if the configuration file matching the image data is not found in 1210, the process may proceed to 1220. In 1220, a scan protocol may be determined. Operation 1220 may be performed by the scan protocol determination unit 410. The scan protocol may include one or more scan conditions and one or more scan ranges, such as a scan speed, a signal strength, a tomography direction and the corresponding number of image layers in a tomography scan, a scan type, a scan time, a scan position, a target scan region, a scan machine parameter, a voltage/current for the scan machine, an irradiation dose, or the like, or any combination thereof.

In some embodiments, the server 150 may acquire the DICOM file of the image data and parse the scan protocol of the image data based on the DICOM file of the image data. The DICOM image file may include the image data and/or the additional information of the image data. The additional information may include the scan protocol.

In some embodiments, there may be one or more preset scan protocols for a target region. In some embodiments, the preset scan protocols may be obtained based on one or more experiments by experienced technicians. In some embodiments, the preset scan protocols may be stored in advance in the storage device and may be called at any time as needed. The preset scan protocols may be generated based on the information relating to the patient's clinical records. The information may include clinical indications, laboratory data, previous imaging reports, other reports from clinical examinations, or the like. The user (e.g. a radiologist) may select the scan protocol suitable for the patient based on the information.

In some embodiments, the server 150 may preset the scan protocol and search the configuration file based on the preset scan protocol, meaning that operation 1210 may be performed after operation 1220. The preset scan protocol may be set in advance based on the information stored in advance (including the patient's gender, weight, age, medical history, biochemical examination information, required image data quality, a scan area, a scan mode, etc.). For example, CT scan parameters may include a tube voltage, a tube current, scan time, a layer thickness, a pitch, a scan volume, or the like. As another example, MRI scan parameters may include the number of diffusion gradient magnetic field, diffusion sensitivity coefficients, pulse repetition interval time, echo time, or the like. In some embodiments, only little or no change (e.g., extension, modification, etc.) may be made to the preset scan protocol, and thus, the configuration file may be searched based on the preset scan protocol. In some embodiments, the scan protocol may include a data structure. The data structure may be used to store one or more parameters required in a scan and/or processing, and/or may be used to record the related device information for completing the scan and/or processing. In some embodiments, the form and specific content of the scan protocol may vary depending on different body sites, different devices, or different individuals.

In 1230, the configuration file may be generated. Operation 1230 may be performed by the configuration file generation sub-unit 422. In some embodiments, the server 150 may generate the configuration file based on the scan protocol determined in 1220. For example, the server 150 may determine the processing algorithm(s) required to be executed based on the scan protocol and/or generate the configuration file according to an execution order of the algorithm(s).

The configuration file generation sub-unit 422 may generate the configuration file based on the image data acquired by the data acquisition module 330. In some embodiments, the configuration file generation sub-unit 422 may extract the image data information in the DICOM image file and/or determine the processing algorithm(s) to be executed based on the image data information. Further, the configuration file generation sub-unit 422 may encode the configuration file into an XML format based on the algorithm name(s) and/or a flow for executing the algorithms to generate a corresponding configuration file of the XML format. In some embodiments, the configuration file generation sub-unit 422 may generate configuration files corresponding to different DICOM image files. Further, the data processing device 120 may execute a corresponding program based on the configuration file to implement an image data processing function. For example, the data processing device 120 may execute one or more algorithms, such as registering, removing a bone and/or a bed board, or the like on a cerebral perfusion image. As another example, the data processing device 120 may perform processing, such as lung segmentation, trachea extraction, rib segmentation, vertebra segmentation, sternum segmentation, or the like on chest CT image data.

The server 150 may construct or configure one or more data source filters, one or more data root filters, one or more processing filters, and connecting pipes between the data source filter(s), the data filter(s), and the processing filter(s) based on the determined image data processing function. The one or more processing filters may be one or more algorithm modules required for implementing the processing function (e.g., image denoising, image enhancement, image splicing, etc.). The server 150 may write the name of the filter(s) and the computer codes corresponding to the pipe(s) in an existing configuration file or a newly-created blank configuration file, so as to generate the configuration file. The generated configuration file may be in the XML format or any other format.

In some embodiments, if the configuration file is found in 1210, or after operation 1230 is performed, the process 1200 may proceed to 1240. In 1240, the data processing pipeline may be constructed based on the configuration file found in 1210 or generated in 1230. Operation 1240 may be performed by the pipeline construction unit 430. Specifically, the server 150 may read the configuration file, assemble the data source filter(s), the data root filter(s), and the pipe(s) based on the configuration file so as to construct the data processing pipeline. The image data may be input to the data processing pipeline through the data source filter(s), may be transmitted to one or more filters through the pipe(s), may be processed by the one or more filters, and finally the processing result may be output by the data root filter(s).

In some embodiments, the data processing device 120 may include one or more filter databases. The filter database may include one or more algorithms which may be used in processing and/or corresponding algorithm source codes. The filter database(s) may be stored in the storage device or any other external data source. The filter database(s) may include one or more filters set in the configuration file, such as a brightness and/or contrast operation filter, a color change sieve, a smoothing filter, a sharpness adjustment filter, a rotary filter, a stretch filter, a compression filter, or the like. In some embodiments, the server 150 may call the same filter for one or more times.

In some embodiments, the server 150 may reconfigure the filter(s). For example, the server 150 may add a new filter or update an existing filter in the filter database(s). As another example, the server 150 may reconfigure the filter as required in the configuration file (e.g., add, change, or delete the filter name in the configuration file, etc.). In some embodiments, the user may send a corresponding instruction to the server 150 through the user interface 201 to reconfigure the filter. In some embodiments, the user may edit a file relating to the filter(s) to reconfigure the filter(s) by the user interface 201. Therefore, the data processing pipeline may be configurable, indicating that the data source filter(s), the data root filter(s), the processing filter(s), and/or the pipe(s) in the data processing pipeline may be editable. In some embodiments, the construction of the data processing pipeline may either extend in depth (i.e., by increasing the number of the filters in a series connection in the data processing pipeline) or extend in width (e.g., by increasing the number of the filters and/or the data root filters in parallel connection in the data processing pipeline).

In 1250, a process may be executed based on the data processing pipeline constructed in 1240. Operation 1250 may be performed by the process execution unit 440. In some embodiments, the server 150 may send a message to the task manager 320 to prompt the task manager 320 to initiate the process. If the process is executed, the server 150 may input data based on the constructed data processing pipeline, process data based on filter algorithms listed in the data processing pipeline, and/or generate a processing result. In some embodiments, the server 150 may execute two or more corresponding processes based on two or more data processing pipelines. In some embodiments, the server 150 may execute two or more data processing processes simultaneously. For example, if memory allows, the server 150 may trigger (or initiate, or start) two or more data processing pipelines simultaneously, execute corresponding processes, and process the same or different data.

In 1270, in the running of the process, it may be determined whether the system is overloaded. Operation 1270 may be performed by the performance monitor 310. The system load may include an overall memory usage rate of the system, an overall CPU occupancy rate of the system, an overall hard disk usage of the system, whether a storage medium works normally, a network speed, a machine failure, or the like. In some embodiments, the information monitored by the performance monitor 310 may be displayed by the user interface 201 and/or the display module 212.

In some embodiments, the performance monitor 310 may check the system load in real time or at regular time intervals. In some embodiments, if the performance monitor 310 monitors that the system is overloaded, the performance monitor 310 may notify the server 150 or the terminal 140 to terminate one or more running processes so as to alleviate the current load of the system. Excessively large system load may refer that the memory usage rate, the CPU occupancy rate, the hard disk usage rate, or the like exceeds one or more preset thresholds (e.g., 50%, 60%, 70%, 80%, 90%, etc.). In some embodiments, if the performance monitor 310 monitors an exception (e.g., the storage medium is unable to read or store data, there is no network speed, or there is a machine failure, etc.), the performance monitor 310 may notify the server 150 or the terminal 140, so that the server 150 or the terminal 140 may take corresponding measures. For example, if the storage medium is damaged, the performance monitor 310 may monitor that the node state of the damaged storage medium is unavailable, and the server 150 may not be able to access the resources stored in the node.

In some embodiments, if it is determined that the system is not overloaded in 1270, the server 150 may execute the process normally, and the process 1200 may proceed to 1280. In 1280, it may be determined whether the data processing is completed. Operation 1280 may be performed by the process monitoring module 322. If the process is not completed, the process may be continued to be executed (e.g., the process 1200 may return to 1270).

In some embodiments, the process monitoring module 322 may check memory usage rate of the process, the CPU occupancy rate of the process, the hard disk usage of the process, the running condition of the process (e.g., the completion rate of the process, the execution time of the process, the remaining time for the execution of the process, whether the process runs normally, etc.), or the like in real time or at regular time intervals.

In some embodiments, the process monitoring module 322 may monitor whether the process runs with an exception, for example, whether the process is aborted, whether the process terminates with an exception. In some embodiments, the process monitoring module 322 may determine the running state of one or more currently running processes based on a corresponding time threshold T. If the execution time of a process exceeds the time threshold T, and a node still does not finish the executing of the process, then the process monitoring module 322 may trigger a response. The response may refer that the process monitoring module 322 notifies the node to close the process. In some embodiments, the process monitoring module 322 may exclude the node and allocate the unfinished process executed by the node to one or more other nodes in candidate available nodes to continue executing the process. In some embodiments, the process monitoring module 322 may collect load information, resource information, and state information of each node, so as to monitor the running state of the processes executed by each node in real time. If a failure occurs in a certain node (e.g., the process executed by the node runs with an exception), the task manager 320 may allocate the process executed by the node to one or more other nodes to continue executing the process, thereby ensuring that the process is not interrupted or reset due to node failures. The task manager 320 may monitor or schedule a load of each node in real time, optimize the resource utilization of each node, and/or improve running speed of the process. In some embodiments, the response may refer that the process monitoring module 322 notifies the process termination module 323 to terminate the process.

In some embodiments, if it is determined that the system is overloaded in 1270, the process 1200 may proceed to 1290. If it is determined that the process is completed in 1280, the process 1200 may proceed to 1290 (e.g., the process may be terminated). In 1290, the process may be terminated. Operation 1290 may be performed by the process termination module 323.

In 1295, a processing result may be generated. Operation 1295 may be performed by the data processing module 350. In some embodiments, operation 1295 may be performed after 1290 (i.e., after the process is terminated), and may be performed before 1290 (i.e., when the process is running). In some embodiments, after the process is terminated, the server 150 may store the processing result and/or an intermediate result in the storage device or other external data sources. In some embodiments, before the processing result is stored, the server 150 may generate one or more folders to store the processing result and/or the intermediate result. In some embodiments, the folder(s) may have the same path as that of data acquired in 1205 or any other path. In some embodiments, the server 150 may delete a result generated by the process that is terminated with an exception.

Figure 13:
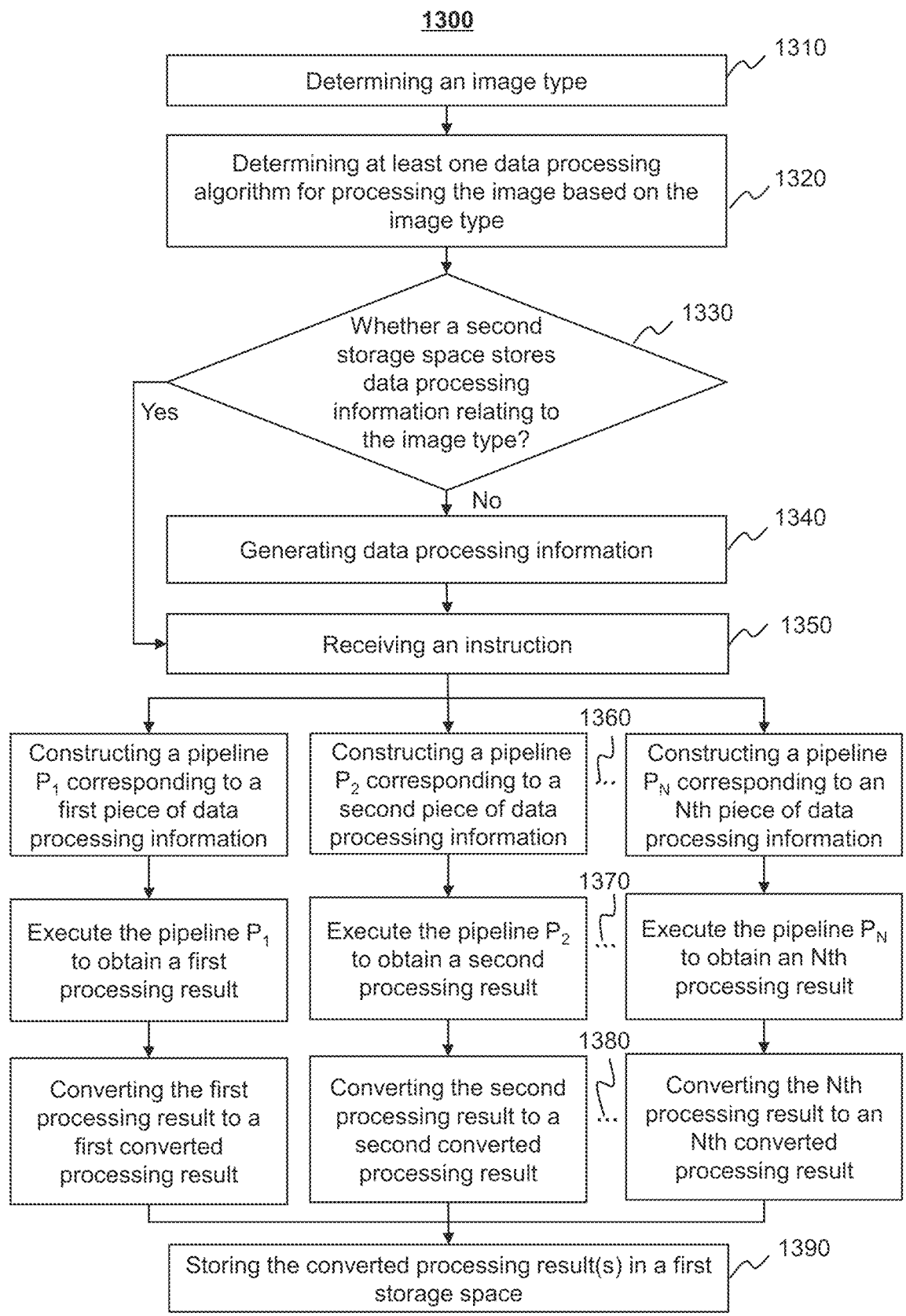
FIG. 13 is a flowchart illustrating an exemplary process for processing image data according to some embodiments of the present disclosure.

FIG. 13 is a flowchart illustrating an exemplary process 1300 for processing image data according to some embodiments of the present disclosure. In some embodiments, the process 1300 may be performed by the data processing module 350.

In 1310, an image type may be acquired. In some embodiments, operation 1310 may be performed by the data acquisition module 330.

In 1320, at least one data processing algorithm for processing the image may be determined based on the image type. Operation 1320 may be performed by the data processing module 350.

In 1330, it may be determined whether a second storage space stores data processing information relating to the image type. If the determination result is YES, operation 1350 may be performed. If the determination result is NO, operation 1340 may be performed. Operation 1330 may be performed by the configuration file judgment sub-unit 423.

If the second storage space does not store the data processing information relating to the image type of the image to be processed, data processing information may be generated in 1340. The data processing information may include one or more data processing algorithms and an execution order of the data processing algorithms. Operation 1340 may be performed by the configuration file generation sub-unit 422.

If the second storage space stores data processing information corresponding to the image type of the image to be processed, the server 150 may process the image using the data processing information stored in the second storage space to obtain the processing result. In 1350, an instruction for indicating the processing of the image may be received. Operation 1350 may be performed by the data processing module 350.

In 1360, one or more data processing pipelines (e.g., the data processing pipeline $P_1$, the data processing pipeline $P_2$, . . . , the data processing pipeline $P_N$, in which N may be an integer greater than or equal to 1) corresponding to the data processing information (e.g., the first piece of data processing information, the second piece of data processing information, . . . , the Nth piece of data processing information) may be constructed based on the data processing information generated in 1340 (or the data processing information obtained in the second storage space) and the instruction received in 1350. Operation 1360 may be performed by the pipeline construction unit 430.

In 1370, each data processing pipeline may be executed to obtain a corresponding processing result (e.g., the first processing result, the second processing result, . . . , the Nth processing result). Operation 1370 may be performed by the process execution unit 440.

In 1380, the processing result(s) (e.g., the first processing result, the second processing result, . . . , the Nth processing result) may be converted to corresponding converted processing result(s) (e.g., the first converted processing result, the second converted processing result, . . . , the Nth converted processing result). Operation 1370 may be performed by the data conversion module 370.

In 1390, the processing result(s) may be stored in a first storage space 160. Operation 1390 may be performed by the data storage module 360.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present disclosure are not limited to that precisely as shown and described.

What is claimed is:

1. A method implemented on at least one machine, each of which has at least one processor and storage for processing medical image data, the method comprising:
   determining a processing instruction;
   acquiring image data based on the processing instruction, the image data corresponding to a DICOM image file, the DICOM image file including a scan protocol, an examination information table, a sequence information table, and an image information table, wherein the examination information table, the sequence information table, and the image information table form an examination-sequence-image three-level data model;
   determining a configuration file based on the image data, the configuration file being configured to guide implementation of the processing instruction and being stored in a form of a DICOM tag, wherein determining the configuration file comprises:
      determining whether there is a matched configuration file by comparing the image data with one or more pieces of information in the DICOM tag; and
      in response to a determination that there is not a matched configuration file, parsing the scan protocol based on the examination-sequence-imaqe three-level data model; and
      generating the configuration file based on the parsed scan protocol, wherein the configuration file includes a name and a connection manner of each of one or more first filters, and the name and the connection manner of each of the one or more first filters are determined based on the parsed scan protocol;
   constructing a data processing pipeline based on the configuration file;
   executing a data processing process based on the data processing pipeline, the data processing process being generated based on the data processing pipeline;
   generating a processing result of the image data based on the executed data processing process; and
   storing the processing result of the image data in a first storage space.

2. The method of claim 1, wherein the determining a processing instruction comprises:
   receiving the processing instruction.

3. The method of claim 1, wherein the determining a processing instruction comprises:
   receiving information relating to a medical image; and
   determining the processing instruction by analyzing the information.

4. The method of claim 1, wherein the one or more first filters including one or more algorithms configured to process the image data, and the connection manner of each of the one or more first filter specifying a connection between the first filter and at least one of another first filter, at least one data source filter, or at least one data root filter, and wherein the constructing the data processing pipeline comprises:
   forming the data processing pipeline based on the one or more first filters, the at least one data source filter, the at least one data root filter, the connection manner, and a plurality of pipes, wherein,
      the data processing pipeline includes the one or more first filters, the at least one data source filter, the at least one data root filter, and the plurality of pipes;
      the plurality of pipes connect the at least one data source filter, the one or more first filters, and the at least one data root filter; and
      at least one of the plurality of pipes perform a data format conversion on the output data from a previous filter connected to the at least one of the plurality of pipes to match the data input format of a next filter connected to the at least one of the plurality of pipes.

5. The method of claim 4, further comprising:
   adding a name of a second filter, modifying the name of at least one of the one or more first filters, or modifying the connection manner in the configuration file.

6. The method of claim 1, further comprising:
   generating a folder based on a storage location of the image data in the first storage space, the folder being used for storing information relating to the data processing process.

7. The method of claim 1, wherein the executing the data processing process comprises:
executing at least two data processing processes simultaneously, wherein the at least two data processing processes are executed independently.

8. The method of claim 1, further comprising:
determining whether the data processing process terminates with an exception; and
in response to a determination that the data processing process terminates with an exception, deleting the processing result of the image data.

9. The method of claim 1, wherein the storing the processing result of the image data in the first storage space, further comprises:
converting the processing result of the image data to obtain a converted result; and
storing the converted result in the first storage space.

10. The method of claim 1, further comprising:
monitoring a memory usage rate or a CPU occupancy rate of the data processing process in real time or at regular time intervals;
displaying the memory usage rate or the CPU occupancy rate on a user interface or a display module; and
terminating the data processing process if the memory usage rate or the CPU occupancy rate exceeds one or more preset thresholds.

11. The method of claim 1, wherein the data processing pipeline comprises:
at least one data source filter;
at least one root filter; and
a plurality of processing filters, wherein the plurality of processing filters are connected by a plurality of pipes forming a series-parallel structure.

12. The method of claim 11, wherein at least one processing filter of the plurality of processing filters is configured with one or more algorithm modules required for implementing one or more processing functions of the configuration file, and the configuration file includes a priority order for executing the algorithm modules.

13. The method of claim 12, wherein the at least one processing filter implements the one or more processing functions or a portion of one of the processing functions.

14. The method of claim 1, further comprising:
presetting the scan protocol based on clinical information of a patient's clinical records, wherein the clinical information of the patient comprises clinical indications, laboratory data, or previous imaging reports.

15. The method of claim 1, wherein
the examination-sequence-image three-level data model is in a form of hierarchical architecture; and
the examination information table, the sequence information table, and the image information table in the examination-sequence-image three-level data model are arranged in an order from upper to lower.

16. A non-transitory computer readable medium including executable instructions, the instructions, when executed by at least one processor, causing the at least one processor to effectuate a method comprising:
determining a processing instruction;
acquiring image data based on the processing instruction, the image data corresponding to a DICOM image file, the DICOM image file including a scan protocol, an examination information table, a sequence information table, and an image information table, wherein the examination information table, the sequence information table, and the image information table form an examination-sequence-image three-level data model;
determining a configuration file based on the image data, the configuration file being configured to guide implementation of the processing instruction and being stored in a form of a DICOM taq, wherein determining the configuration file comprises:
determining whether there is a matched configuration file by comparing the image data with one or more pieces of information in the DICOM tag; and
in response to a determination that there is not a matched configuration file, parsing the scan protocol based on the examination-sequence-imaqe three-level data model; and
generating the configuration file based on the parsed scan protocol, wherein the configuration file includes a name and a connection manner of each of one or more first filters, and the name and the connection manner of each of the one or more first filters are determined based on the parsed scan protocol;
constructing a data processing pipeline based on the configuration file;
executing a data processing process based on the data processing pipeline, the data processing process being generated based on the data processing pipeline;
generating a processing result of the image data based on the executed data processing process; and
storing the processing result of the image data in a first storage space.

17. A system comprising:
at least one processor; and
a storage configured to store instructions, the instructions, when executed by the at least one processor, causing the system to effectuate a method comprising:
determining a processing instruction;
acquiring image data based on the processing instruction, the image data corresponding to a DICOM image file, the DICOM image file including a scan protocol, an examination information table, a sequence information table, and an image information table, wherein the examination information table, the sequence information table, and the image information table form an examination-sequence-image three-level data model;
determining a configuration file based on the image data, the configuration file being configured to guide implementation of the processing instruction and being stored in a form of a DICOM tag, wherein determining the configuration file comprises:
determining whether there is a matched configuration file by comparing the image data with one or more pieces of information in the DICOM tag; and
in response to a determination that there is not a matched configuration file, parsing the scan protocol based on the examination-sequence-image three-level data model; and
generating the configuration file based on the parsed scan protocol, wherein the configuration file includes a name and a connection manner of each of one or more first filters, and the name and the connection manner of each of the one or more first filters are determined based on the parsed scan protocol;
constructing a data processing pipeline based on the configuration file;
executing a data processing process based on the data processing pipeline, the data processing process being generated based on the data processing pipeline;
generating a processing result of the image data based on the executed data processing process; and storing the processing result of the image data in a first storage space.

18. The system of claim 17, wherein the determining whether there is a matched configuration file by comparing the image data with one or more pieces of information in the DICOM taq comprises:
   determining whether there is a matched configuration file in a second storage space by comparing the image data with the one or more pieces of information in the DICOM tag; and
   wherein the determining the configuration file further comprises:
   in response to a determination that there is a matched configuration file in the second storage space, determining the matched configuration file as the configuration file; and
   in response to a determination that there is not a matched configuration file in the second storage space, storing the generated configuration file in the second storage space.

19. The system of claim 17, the one or more first filters including one or more algorithms configured to process the image data, and the connection manner of each of the one or more first filter specifying a connection between the first filter and at least one of another first filter, at least one data source filter, or at least one data root filter, and wherein the constructing the data processing pipeline comprises:
   forming the data processing pipeline based on the one or more first filters, the at least one data source filter, the at least one data root filter, the connection manner, and a plurality of pipes, wherein,
   the data processing pipeline includes the one or more first filters, the at least one data source filter, the at least one data root filter, and the plurality of pipes; and
   the plurality of pipes connect the at least one data source filter, the one or more first filters, and the at least one data root filter; and
   at least one of the plurality of pipes perform a data format conversion on the output data from a previous filter connected to the at least one of the plurality of pipes to match the data input format of a next filter connected to the at least one of the plurality of pipes.

20. The system of claim 19, wherein each of the one or more first filters is configured with an algorithm for processing the image data.

* * * * *